US011752216B2

(12) United States Patent
Park et al.

(10) Patent No.: US 11,752,216 B2
(45) Date of Patent: Sep. 12, 2023

(54) INSULIN ANALOG COMPLEX WITH REDUCED AFFINITY FOR INSULIN RECEPTOR AND USE THEREOF

(71) Applicant: HANMI PHARM. CO., LTD., Hwaseong-si (KR)

(72) Inventors: Young Jin Park, Hwaseong-si (KR); In Young Choi, Hwaseong-si (KR); Sung Youb Jung, Hwaseong-si (KR); Se Chang Kwon, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 16/495,884

(22) PCT Filed: Mar. 23, 2018

(86) PCT No.: PCT/KR2018/003489
§ 371 (c)(1),
(2) Date: Sep. 20, 2019

(87) PCT Pub. No.: WO2018/174668
PCT Pub. Date: Sep. 27, 2018

(65) Prior Publication Data
US 2020/0101171 A1 Apr. 2, 2020

(30) Foreign Application Priority Data
Mar. 23, 2017 (KR) .................. 10-2017-0037101

(51) Int. Cl.
| C07K 14/62 | (2006.01) |
| A61K 47/68 | (2017.01) |
| A61K 47/60 | (2017.01) |
| A61P 3/10 | (2006.01) |
| A61K 38/00 | (2006.01) |

(52) U.S. Cl.
CPC .......... *A61K 47/6883* (2017.08); *A61K 47/60* (2017.08); *A61P 3/10* (2018.01); *C07K 14/62* (2013.01); *A61K 38/00* (2013.01)

(58) Field of Classification Search
CPC ............................. A61K 38/28; C07K 14/605
See application file for complete search history.

(56) References Cited

U.S. PATENT DOCUMENTS

| 5,175,145 A | 12/1992 | Cooper |
| 5,422,339 A | 6/1995 | Eisenbarth et al. |
| 5,424,286 A | 6/1995 | Eng |
| 5,716,927 A | 2/1998 | Balschmidt et al. |
| 6,403,764 B1 | 6/2002 | Dubaquie et al. |
| 7,736,653 B2 | 6/2010 | Kim et al. |
| 7,790,677 B2 | 9/2010 | Zimmerman et al. |
| 8,476,230 B2 | 7/2013 | Song et al. |
| 8,691,759 B2 | 4/2014 | Madsen et al. |
| 8,703,701 B2 | 4/2014 | DiMarchi |
| 9,018,161 B2 | 4/2015 | Nielsen et al. |
| 9,165,768 B2 | 10/2015 | Kang |
| 9,260,502 B2 | 2/2016 | Nielsen et al. |
| 9,341,445 B2 | 5/2016 | de Haas et al. |
| 9,422,349 B2 | 8/2016 | Jung et al. |
| 9,526,764 B2 | 12/2016 | Werner et al. |
| 9,528,180 B2 | 12/2016 | Becker et al. |
| 9,669,073 B2 | 6/2017 | Kim et al. |
| 2005/0288248 A1 | 12/2005 | Pan et al. |
| 2006/0241019 A1 | 10/2006 | Bridon et al. |
| 2009/0306337 A1 | 12/2009 | Madsen et al. |
| 2010/0105877 A1 | 4/2010 | Song et al. |
| 2010/0216692 A1 | 8/2010 | Brunner-Schwarz et al. |
| 2011/0077197 A1 | 3/2011 | Habermann et al. |
| 2011/0152185 A1 | 6/2011 | Plum et al. |
| 2011/0257091 A1 | 10/2011 | DiMarchi et al. |
| 2012/0021978 A1 | 1/2012 | Werner et al. |
| 2012/0071402 A1 | 3/2012 | Madsen et al. |
| 2012/0100141 A1 | 4/2012 | Herring et al. |
| 2012/0184488 A1 | 7/2012 | Weiss |
| 2013/0028918 A1 | 1/2013 | Song et al. |
| 2013/0122023 A1 | 5/2013 | Woo et al. |
| 2014/0120120 A1 | 5/2014 | Woo et al. |
| 2014/0212440 A1 | 7/2014 | Jung et al. |
| 2015/0190528 A1 | 7/2015 | Lim et al. |
| 2016/0000931 A1 | 1/2016 | Jang et al. |
| 2016/0008483 A1 | 1/2016 | Hwang et al. |
| 2017/0066811 A1 | 3/2017 | Kim et al. |
| 2017/0101455 A1 | 4/2017 | Jung et al. |
| 2017/0143802 A1 | 5/2017 | Kim et al. |
| 2017/0196943 A1 | 7/2017 | Jung et al. |
| 2018/0282388 A1 | 10/2018 | Kim et al. |
| 2018/0291077 A1 | 10/2018 | Choi et al. |
| 2019/0600593 | 10/2019 | Choi et al. |

FOREIGN PATENT DOCUMENTS

| CL | 1235-2003 | 4/2004 |
| CL | 0018-2009 | 6/2009 |
| CL | 201603075 | 11/2016 |
| CN | 1571676 A | 1/2005 |
| CN | 1635900 A | 7/2005 |

(Continued)

OTHER PUBLICATIONS

Extended European Search Report dated May 7, 2020 in European Application No. 17853478.0.
Wells, "Additivity of Mutational Effects m Proteins", Biochemistry, vol. 29, No. 37, Sep. 18, 1990, pp. 8509-8517 (9 pages total).
Senshang Lin et al., "Comparative Pharmacokinetic and Pharmacodynamic Studies of Human Insulin and Analogues in Chronic Diabetic Yucatan Minipigs," The Journal of Pharmacology and Experimental Therapeutics, 1998, pp. 959-966, vol. 286, No. 2.
Ulla Ribel et al., "Equivalent In Vivo Biological Activity of Insulin Analogues and Human Insulin Despite Different In Vitro Potencies," Diabetes, Sep. 1990, pp. 1033-1039, vol. 39.
Jens Brange et al., "Monomeric Insulins and Their Experimental and Clinical Implications," Diabetes Care, Sep. 1990, pp. 923-954, vol. 13, No. 9.

(Continued)

*Primary Examiner* — Gyan Chandra
(74) *Attorney, Agent, or Firm* — Sughrue Mion, PLLC

(57) ABSTRACT

The present invention relates to an insulin analog conjugate and use thereof.

19 Claims, 9 Drawing Sheets
Specification includes a Sequence Listing.

(56) References Cited

FOREIGN PATENT DOCUMENTS

| | | |
|---|---|---|
| CN | 101743252 A | 6/2010 |
| CN | 101861333 A | 10/2010 |
| CN | 102256618 A | 11/2011 |
| CN | 102711805 A | 10/2012 |
| CN | 103596584 A | 2/2014 |
| CN | 103596595 A | 2/2014 |
| CN | 103732616 A | 4/2014 |
| CN | 103736082 A | 4/2014 |
| DE | 25 36 040 A1 | 2/1977 |
| DE | 10227232 A1 | 1/2004 |
| DE | 102008003568 A1 | 7/2009 |
| DE | 102008025008 A1 | 11/2009 |
| EA | 201690116 A1 | 7/2016 |
| EP | 2017288 A1 | 1/2009 |
| EP | 2279758 A2 | 2/2011 |
| EP | 2700654 A1 | 2/2014 |
| EP | 2963056 A1 | 1/2016 |
| EP | 3 028 399 A1 | 6/2016 |
| JP | 4-502465 A | 5/1992 |
| JP | 2007-91747 A | 4/2007 |
| JP | 2007-537992 A | 12/2007 |
| JP | 2008-506635 A | 3/2008 |
| JP | 2009-504169 A | 2/2009 |
| JP | 2010-504087 A | 2/2010 |
| JP | 2010-522559 A | 7/2010 |
| JP | 2010-533671 A | 10/2010 |
| JP | 2011-512856 A | 4/2011 |
| JP | 2011-515358 A | 5/2011 |
| JP | 2012-62311 A | 3/2012 |
| JP | 2012-229214 A | 11/2012 |
| JP | 2013-533864 A | 8/2013 |
| JP | 2015-509950 A | 4/2015 |
| KR | 10-2005-0121748 A | 12/2005 |
| KR | 10-0725315 B1 | 6/2007 |
| KR | 10-2010-0111683 A | 10/2010 |
| KR | 10-2011-0084956 A | 7/2011 |
| KR | 10-2011-0092253 A | 8/2011 |
| KR | 10-1058209 B1 | 8/2011 |
| KR | 10-1058290 B1 | 8/2011 |
| KR | 10-2011-0111267 A | 10/2011 |
| KR | 10-2011-0134210 A | 12/2011 |
| KR | 10-2011-0137819 A | 12/2011 |
| KR | 1020110134209 A | 12/2011 |
| KR | 10-2012-0135123 A | 12/2012 |
| KR | 10-2012-0137271 A | 12/2012 |
| KR | 10-2012-0139579 A | 12/2012 |
| KR | 10-1231431 B1 | 2/2013 |
| KR | 10-1324828 B1 | 11/2013 |
| KR | 10-1330868 B1 | 11/2013 |
| KR | 10-2014-0006938 A | 1/2014 |
| KR | 10-2014-0022909 A | 2/2014 |
| KR | 10-2014-0106452 A | 9/2014 |
| KR | 10-2015-0087130 A | 7/2015 |
| KR | 10-2015-0138101 A | 12/2015 |
| KR | 10-2016-0001391 A | 1/2016 |
| KR | 10-2016-0007295 A | 1/2016 |
| TW | 201204382 A1 | 2/2012 |
| TW | 201410704 A | 3/2014 |
| TW | 201520224 A | 6/2015 |
| WO | 96/32478 A1 | 10/1996 |
| WO | 97/34631 A1 | 9/1997 |
| WO | 2008/034881 A1 | 3/2008 |
| WO | 2008/145721 A2 | 12/2008 |
| WO | 2009/022005 A1 | 2/2009 |
| WO | 2009/063072 A2 | 5/2009 |
| WO | 2009112583 A2 | 9/2009 |
| WO | 2009/129250 A2 | 10/2009 |
| WO | 2010/043566 A3 | 4/2010 |
| WO | 2010/080606 A1 | 7/2010 |
| WO | 2010/080609 A1 | 7/2010 |
| WO | 2011/028813 A2 | 3/2011 |
| WO | 2011/075606 A2 | 6/2011 |
| WO | 2011122921 A2 | 10/2011 |
| WO | 2012/015692 A2 | 2/2012 |
| WO | 2012/098462 A1 | 7/2012 |
| WO | 2012/165915 A2 | 12/2012 |
| WO | 2012/167251 A1 | 12/2012 |
| WO | 2012/169798 A2 | 12/2012 |
| WO | 2012/173422 A1 | 12/2012 |
| WO | 2013/110069 A1 | 7/2013 |
| WO | 2013/133667 A1 | 9/2013 |
| WO | 2014/017843 A1 | 1/2014 |
| WO | 2014/017845 A2 | 1/2014 |
| WO | 2014/017847 A1 | 1/2014 |
| WO | 2014/017849 A1 | 1/2014 |
| WO | 2014/049610 A2 | 4/2014 |
| WO | 2014/073842 A1 | 5/2014 |
| WO | 2014073845 A1 | 5/2014 |
| WO | 2014/133324 A1 | 9/2014 |
| WO | 2015/013745 A1 | 2/2015 |
| WO | 2015108398 A1 | 7/2015 |
| WO | 2015/183038 A1 | 12/2015 |
| WO | 2015199511 A1 | 12/2015 |
| WO | 2016/006963 A1 | 1/2016 |
| WO | 2017/052305 A1 | 3/2017 |

OTHER PUBLICATIONS

International Search Report of PCT/KR2018/003489 dated Oct. 29, 2018.
U.S. Appl. No. 16/335,490, filed Mar. 21, 2019, Choi et al.
U.S. Appl. No. 15/990,495, filed May 25, 2018, Kim et al.
U.S. Appl. No. 15/250,459, filed Aug. 26, 2016, Kim et al.
U.S. Appl. No. 15/113,027, filed Jul. 20, 2016, Jung et al.
U.S. Appl. No. 15/313,501, filed Nov. 22, 2016, Kim et al.
U.S. Appl. No. 14/769,495, filed Aug. 21, 2015, Hwang et al.
U.S. Appl. No. 15/315,020, filed Nov. 30, 2016, Jung et al.
United States Patent and Trademark Office Restriction Requirement dated May 30, 2019 in U.S. Appl. No. 15/983,923.
R. Vigneri, et al., "Insulin and its analogs: actions via insulin and IGF receptors", Acta Diabetol, 2010, pp. 271-278, vol. 47, No. 4.
NCBI, "insulin preproprotein [*Homo sapiens*]", NCBI Reference Sequence: NP_000198.1, Feb. 17, 2013, [online]<http://www.ncbi.nlm.nih.gov/protein/4557671?sat=17&satkey=22757282> retrieved on Mar. 31, 2014, p. 2.
United States Patent and Trademark Office Restriction Requirement dated Jan. 10, 2018 in U.S. Appl. No. 15/315,020.
United States Patent and Trademark Office Notice of Allowance dated Sep. 7, 2018 in U.S. Appl. No. 15/315,020.
International Searching Authority, International Search Report of PCT/KR2017/010504 dated Jan. 31, 2018.
International Searching Authority, International Search Report for PCT/KR2014/001593 dated May 22, 2014.
International Searching Authority, Written Opinion of the International Search Authority for PCT/KR2014/001593 dated May 22, 2014.
Chile Patent Office, Communication dated Aug. 22, 2016, issued in Chilean Application No. 2015-002330.
European Patent Office; Communication dated Nov. 30, 2016, in European Application No. 14757629.2.
Colombian Patent Office; Communication dated Nov. 8, 2016, in Columbian application No. 15227010.
European Patent Office; Communication dated May 10, 2017, in European application No. 14757629.2.
Chilean Patent Office, Communication dated Jul. 13, 2017 by the Chilean Patent Office in Chilean Patent Application No. 201601844.
European Patent Office, Communication dated Sep. 20, 2017 by the European Patent Office in Application No. EP 15 73 7856.3.
Authier F. et al. (1998) "Uptake and Metabolic Fate of [His$^{48}$, His$^{B4}$, Glu$^{B10}$, His$^{B27}$] Insulin in Rat Liver In Vivo," Biochem J. 332;421-30.
Duckworth, W.C. et al. (Oct. 1998). "Insulin Degradation: Process and Potential," Endocr Rev. 19(5):608-24.
Valera, M. M. et al. (Dec. 2003). "Insulin Clearance in Obesity," J Am Coll Nutr. 22(6):487-93, Abstract Only.
United States Patent and Trademark Office communication dated Sep. 14, 2017 in U.S. Appl. No. 15/250,459.

(56) References Cited

OTHER PUBLICATIONS

UniProtKB A6XGL2, pp. 1-5. Integrated in UniProtKB/TrEMBL Aug. 21, 2007.
Keller, D. et al. (2001). "Flexibility and Bioactivity of Insulin: an NMR Investigation of the Solution Structure and Folding of an Unusually Flexible Human Insulin Mutant with Increased Biological Activity," Biochemistry 40(35):10732-10740.
NCBI, Genbank AAA72172.1, (Apr. 27, 1993)/ "Synthetic Preproinsulin [synthetic construct] NCBI," located at https://www.ncbi.nlm.nih.gov/protein/AAA72172.1?report=gpwithparts&log$=seqview, last visited on Jun. 20, 2017, 1 page.
NCBI, Genbank AKI70564.1 (Jun. 1, 2015). "INS, Partial [synthetic construct]" located at <https://www.ncbi.nlm.nih.goV/protein/AKI70564.1?report= gpwithparts&log$=seqview> last visited on Jun. 20, 2017, 2 pages.
NCBI, Genbank NM_001291897.1, (May 13, 2015). "*Homo Sapiens* Insulin (INS), Transcript Variant 4, mRNA," located at < https://www.ncbi.nlm.nih.gov/nuccore/NM-001291897.1?report=gpwithparts&logS=seqview&sat=4&satkey=139944924>, last visited on Jun. 20, 2017, 3 pages.
Yampolsky et al., "The Exchangeability of Amino Acids in Proteins," Genetics, 170: 1459-1472, 2005.
Rudinger J., "Characteristics of the Amino Acids as Components of a Peptide Hormone Sequence," Peptide Hormones, J.A. Parsons Edition, University Park Press, Jun. 1976, pp. 1-7. (8 pages total).
"Designing Custom Peptides," from SIGMA Genosys, pp. 1-2. Accessed Dec. 16, 2004.
Schinzel R., Drueckes P., "The Phosphate Recognition Site of *Escherichia coli* Maltodextrin Phosphorylase," FEBS, Jul. 1991. 286(1,2): 125-128.
Berendsen HJC, "A Glimpse of the Holy Grail?" Science, 1998, 282: 642-643.
Voet D, Voet JG, Biochemistry, Second Edition, John Wiley & Sons, Inc., 1995, pp. 235-241. (9 pages).
Ngo J.T., Marks J, Karplus M., "Computational Complexity, Protein Structure Prediction, and the Levinthal Paradox," The Protein Folding Problem and Tertiary Structure Prediction, K. Merc Jr. and S. Le Grand Editors, 1994, pp. 491-495.
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.
Betts et al., "Amino Acid Properties and Consequences of Substitutions," Bioinformatics for Geneticists, Chapter 14, John Wiley & Sons, Ltd., 2003, pp. 289-316.
Jørgensen, A. et al. (Apr. 1996). "Solution Structure of the Superactive Monomeric Des-[Phe(B25)] Human Insulin Mutant: Elucidation of the Structural Basis for the Monomerization of Des-[Phe(B25)] Insulin and the Dimerization of Native Insulin," J. Mol. Biol., 257(3):684-699.
Uhlmann, E. et al. (Jun. 1990). "Antisense Oligonucleotides: A New Therapeutic Principle," Chemical Reviews 90(4):543-584.
United States Patent and Trademark Office Non-Final Office Action dated Sep. 8, 2017 in U.S. Appl. No. 15/313,501.
Martin Lorenz et al., "Recent progress and future options in the development of GLP-1 receptor agonists for the treatment of diabesity", Bioorganic & Medicinal Chemistry Letters, 2013, pp. 4011-4018, vol. 23, No. 14.
International Searching Authority, International Search Report of PCT/KR2015/005455 dated Aug. 24, 2015 [PCT/ISA/210].
International Searching Authority, Written Opinion of PCT/KR2015/005455 dated Aug. 24, 2015 [PCT/ISA/237]'.
Colombian Patent Office; Communication dated Aug. 24, 2017, in Colombian application No. 15227010.
Taiwanese Intei I Fctual Property Office; Communication dated Sep. 11, 2017 in application No. 103106674.
Intfi I Fctual Property Office of Singapore, Communication dated Oct. 3, 2017 in application No. 11201609564T.
European Patent Office, Communication dated Nov. 10, 2017 in application No. 15799334.6.
Fosgerau et al., "Combination of Long-Acting Insulin with the Dual GluGLP-1 Agonist ZP2929 Causes Improved Glycemic Control without Body Weight Gain in db/db Mice", 1527-P, Diabetes (Suppl 1), vol. 60, 2011, p. A418, XP-002775063.
European Patent Office; Communication dated Nov. 17, 2017 in application No. 15799077.1.
United States Patent and Trademark Office; Notice of Allowance dated Feb. 26, 2018 in U.S. Appl. No. 15/250,459.
United States Patent and Trademark Office; Non-Final Office Action dated Jan. 16, 2018 in U.S. Appl. No. 15/113,027.
United States Patent and Trademark Office; Final Rejection dated Mar. 8, 2018 in U.S. Appl. No. 15/313,501.
Japanese Patent Office; Communication dated Jan. 16, 2018 in Japanese application No. 2015-559199.
Saudi Arabian Patent Office, Communication dated Apr. 30, 2016 issued in Application No. 515360933.
Intellectual Property Office of Singapore; Communication dated Jan. 29, 2018 in application No. 11201609872Y.
United States Patent and Trademark Office; Non-Final Office Action dated Apr. 17, 2018 in U.S. Appl. No. 15/315,020.
Colombian Patent and Trademark Office; communication dated Feb. 16, 2018, in Colombian application No. NC2016/0004794.
Kristensen et al., "Alanine Scanning Mutagenesis of Insulin," J. Biol. Chem. 272:12978-12983 (1997).
Chen et al., "Four new monomeric insulins obtained by alanine scanning the dimer-forming surface of the insulin molecule," Protein Eng'g 13:779-782 (2000).
Nakagawa et al., "Chiral Mutagenesis of Insulin, Contribution of the B20-B23 β-turn to activity and stability," J. Biol. Chem. 281: 22386-22396, (2006).
Chu et al., "The A14 Position of Insulin Tolerates Considerable Structural Alterations with Modest Effects on the Biological Behavior of the Hormone," J. Prot. Chem. 11:571-577 (1992).
Mohan, "Which insulin to use? Human or animal?," Curr. Sci. 83:1544-1547 (2002).
Chinese Patent and Trademark Office; communication dated Mar. 1, 2018, in Chinese Patent Application No. 201480006998.4.
Chilean Patent Office; Communication dated May 29, 2018 issued in Chilean Application No. 201603069.
Ukraine Patent Office; Communication dated Jul. 2, 2018 in application No. 12469/3A/18.
Intellectual Property Office of Taiwan; Communication dated Jun. 29, 2018 in application No. 106143717.
Intellectual Property Office of the Dominican Republic; Communication dated Jul. 26, 2018 in application No. P2016-176.
Japanese Patent Office; Communication dated Sep. 11, 2018 in application No. 2015-559199.
Glendorf et al., "Engineering of Insulin Receptor Isoform-Selective Insulin Analogues", PLOS One, vol. 6, Issue 5, e20288, May 2011, 7 pages total.
Chilean Patent Office; Communication dated Nov. 14, 2018 issued in application No. 201603069.
Japanfsf Patent Office: Communication dated Nov. 13, 2018 in application No. 2016-564933.
Japanese Patent Office; Communication dated Mar. 5, 2019 in application No. 2016-569949.
Intellectual Property Office of Taiwan; Communication dated May 1, 2019 in application No. 104117389.
Intellectual Property Office of Singapore; Communication dated Apr. 5, 2019 in application No. 11201609872Y.
Wolfgang Glaesner et al., "Engineering and characterization of the long-acting glucagon-like peptide-1 analogue LY2189265, an Fc fusion protein", Diabetes/Metabolism Research and Reviews, vol. 26, 2010, pp. 287-296.
"CADTH Optimal Use Report: Combination Use of Insulin and Incretins in Type 2 Diabetes", Canadian Agency for Drugs and Technologies in Health, vol. 3, Issue 1C, Jul. 2013, pp. i-ii, 1-18 (22 pages total).
Fabio Selis et al., "Enzymatic mono-pegylation of glucagon-like peptide 1 towards long lasting treatment of type 2 diabetes", Results in Pharma Sciences 2, Elsevier, 2012, pp. 58-65.

(56) References Cited

OTHER PUBLICATIONS

C. Schmid et al., "Increased insulin dose requirement of long-acting insulin analogues in obese patients with type 2 diabetes", Diabetologia, vol. 52, 2009, pp. 2668-2669.
Bhat et al., "A novel GIP-oxyntomodulin hybrid peptide acting through GIP, glucagon and GLP-1 receptors exhibits weight reducing and anti-diabetic properties", Biochem Pharmacol, Jun. 1, 2013,vol. 85 No. 11, pp. 1655-1662.
Intellectual Property Office of Singapore; Communication dated Jul. 15, 2019 in application No. 11201802523X.
Ministry of Law and Human Rights Republic of Indonesia; Communication dated Jun. 12, 2019 in application No. P00201608768.
Intellectual Property Office of Taiwan; Communication dated May 13, 2019 in application No. 104117391.
European Patent Office; Communication dated Jul. 19, 2019 in application No. 16842233.5.
Pocai, "Unraveling oxyntomodulin, GLPTs enigmatic brother", Journal of Endocrinology, vol. 215, No. 3, pp. 335-346, Sep. 27, 2012.
Hinds et al., "Effects of PEG conjugation on insulin properties", Advanced Drug Delivery Reviews, vol. 54, No. 4, pp. 505-530, 2002.
Thibaudeau et al., "Synthesis and Evaluation of Insulin—Human Serum Albumin Conjugates", Bioconjugate Chemistry, American Chemical Society, vol. 16, No. 4, pp. 1000-1008, Jun. 25, 2005.
European Patent Office, Communication dated Sep. 20, 2017 by the European Patent Officer in application No. EP 15 73 7856.3.
United States Patent and Trademark Office communication dated Jul. 19, 2017 in U.S. Appl. No. 14/769,495.
United States Patent and Trademark Office communication dated Jan. 17, 2017 in U.S. Appl. No. 14/769,495.
United States Patent and Trademark Office communication dated Apr. 5, 2018 in U.S. Appl. No. 14/769,495.
United States Patent and Trademark Office communication dated Jul. 17, 2018 in U.S. Appl. No. 15/113,027.
Intellectual Property Office of Taiwan; Communication dated Jul. 2, 2018 in application No. 106143717.
Japanese Patent Office; Communication dated Jul. 4, 2019 in application No. 2016-570276.
United States Patent and Trademark Office Notice of Allowance dated Jan. 15, 2020 in U.S. Appl. No. 15/990,495.
United States Patent and Trademark Office Non-Final Office Action dated Aug. 23, 2019 in U.S. Appl. No. 15/990,495.
United States Patent and Trademark Office Restriction Requirement dated Apr. 22, 2019 in U.S. Appl. No. 15/990,495.
United States Patent and Trademark Office; Notice of Allowance dated Nov. 8, 2018 in U.S. Appl. No. 15/113,027.
United States Patent and Trademark Office; Final Office Action dated Jul. 17, 2018 in U.S. Appl. No. 15/113,027.
United States Patent and Trademark Office Restriction Requirement dated Jul. 18, 2017 in U.S. Appl. No. 15/113,027.
United States Patent and Trademark Office Notice of Allowance dated Aug. 7, 2018 in U.S. Appl. No. 15/313,501.
United States Patent and Trademark Office Restriction Requirement dated Apr. 20, 2020 in U.S. Appl. No. 1516/335,490.
Baudys et al., "Extending Insulin Action in Vivo by Conjugation to Carboxymethyl Dextran", Bioconjugate Chem., 1998, 9, 176-183.
Cockram CS et al., "The Biological Properties of Insulins with Tyrosine Replaced by Phenylalanine at Positions 14 and 19 of the A Chain" Diabet. Med., 1985, vol. 2, No. 4, p. 241-244 (4 pages total).
Karounos, D. G. et al., "Metabolically inactive insulin analog prevents type I diabetes in prediabetic NOD mice", J. Clin. Invest., 1997, vol. 100, No. 6, pp. 1344-1348.
Gauguin, L. et al., "Structural Basis for the Lower Affinity of the Insulin-like Growth Factors for the Insulin Receptor", J. Biol. Chem., 2008, vol. 283, No. 5, pp. 2604-2613.
Glendorf et al., "Importance of the Solvent-Exposed Residues of the Insulin B Chain α-Helix for Receptor Binding", Biochemistry, 2008, vol. 47, No. 16, pp. 4743-4751 (9 pages total).
Affholter et al., "Identification of Residues in the Insulin Molecule Important for Binding to Insulin-Degrading Enzyme", Biochemistry, 1990, vol. 29, No. 33, pp. 7727-7733 (7 pages total).
Fosgerau et al., "The new glucagon-GLP-1 dual agonist ZP2929 in combination with long-acting insulin improves glycemic control without causing weight gain in db/db mice", American Diabetes Association (ADA,) 71st Scientific Session, Jun. 24-28, 2011, 1 page.
Kobayashi, "Diabetes: Diagnosis and Treatment Progress. III. Recent Topics Surrounding Diabetes. 1. Insulin gene and abnormality thereof", Nihon Pharmaceutical Society, Aug. 10, 1991, vol. 80, No. 8, pp. 75-79 (7 pages total).
Yoram Shechter et al., "Albumin-lnsulin Conjugate Releasing Insulin Slowly under Physiological Conditions: A New Concept for Long-Acting Insulin", Bioconjugate Chem., 2005, vol. 16, No. 4, pp. 913-920 (8 pages).
Epstein, "Non-randomness of Amino-acid Changes in the Evolution of Homologous Proteins", Nature Publishing Group, vol. 215, Jul. 22, 1967, pp. 355-359.

[Figure 1]
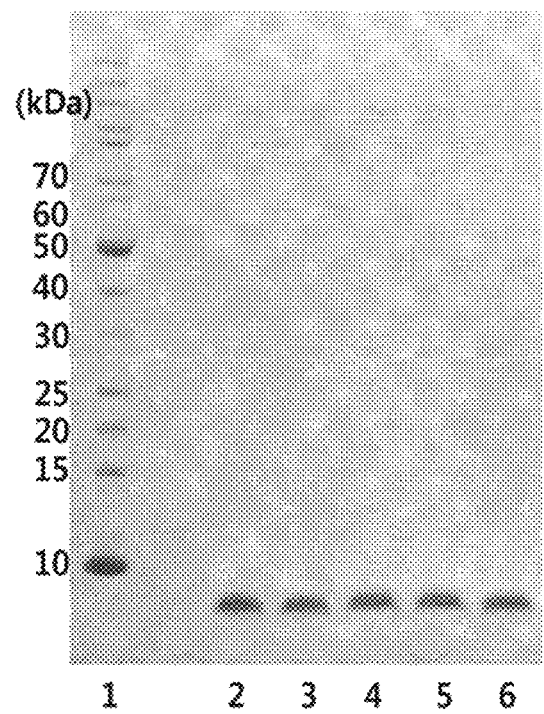

[Figure 2a]
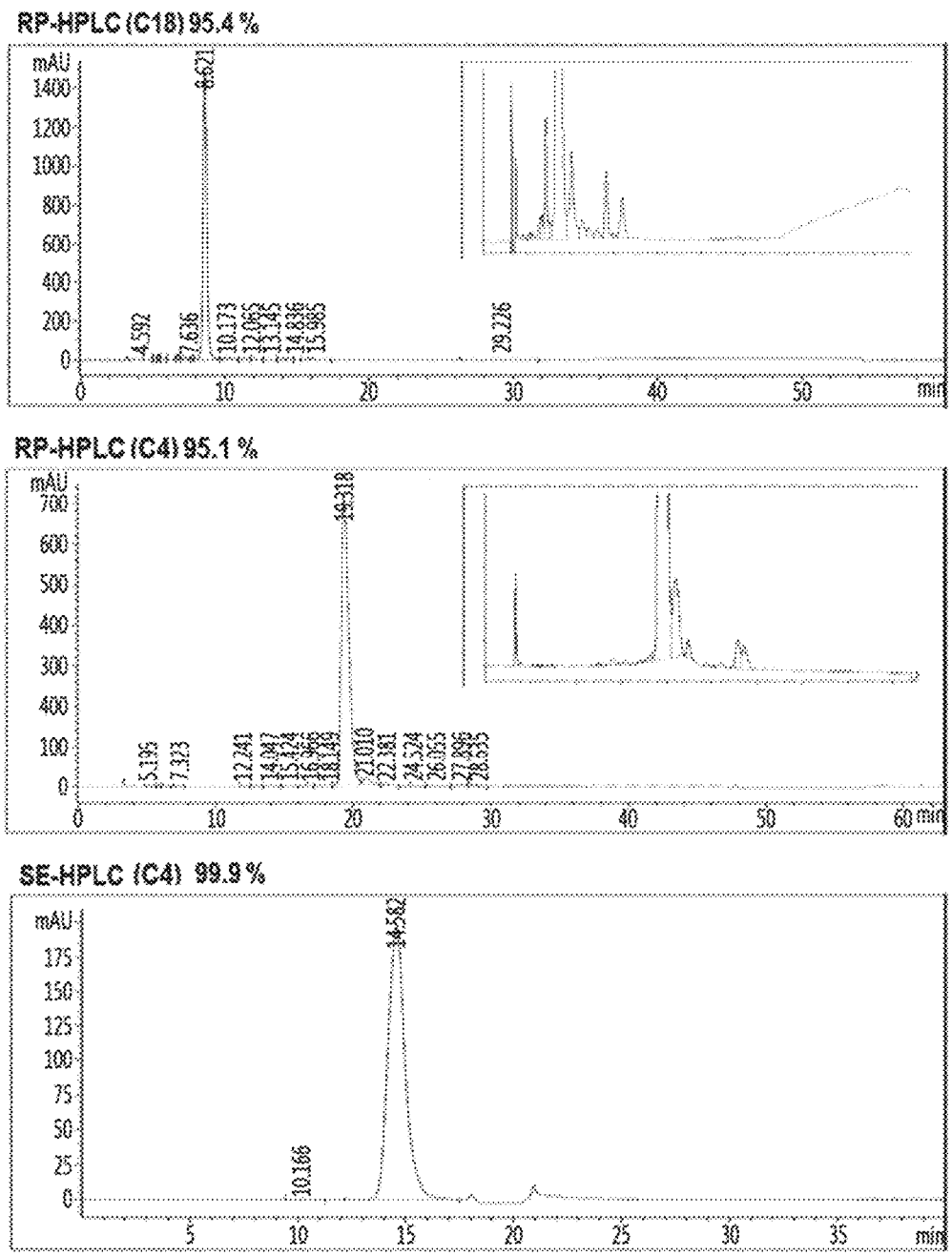

[Figure 2b]
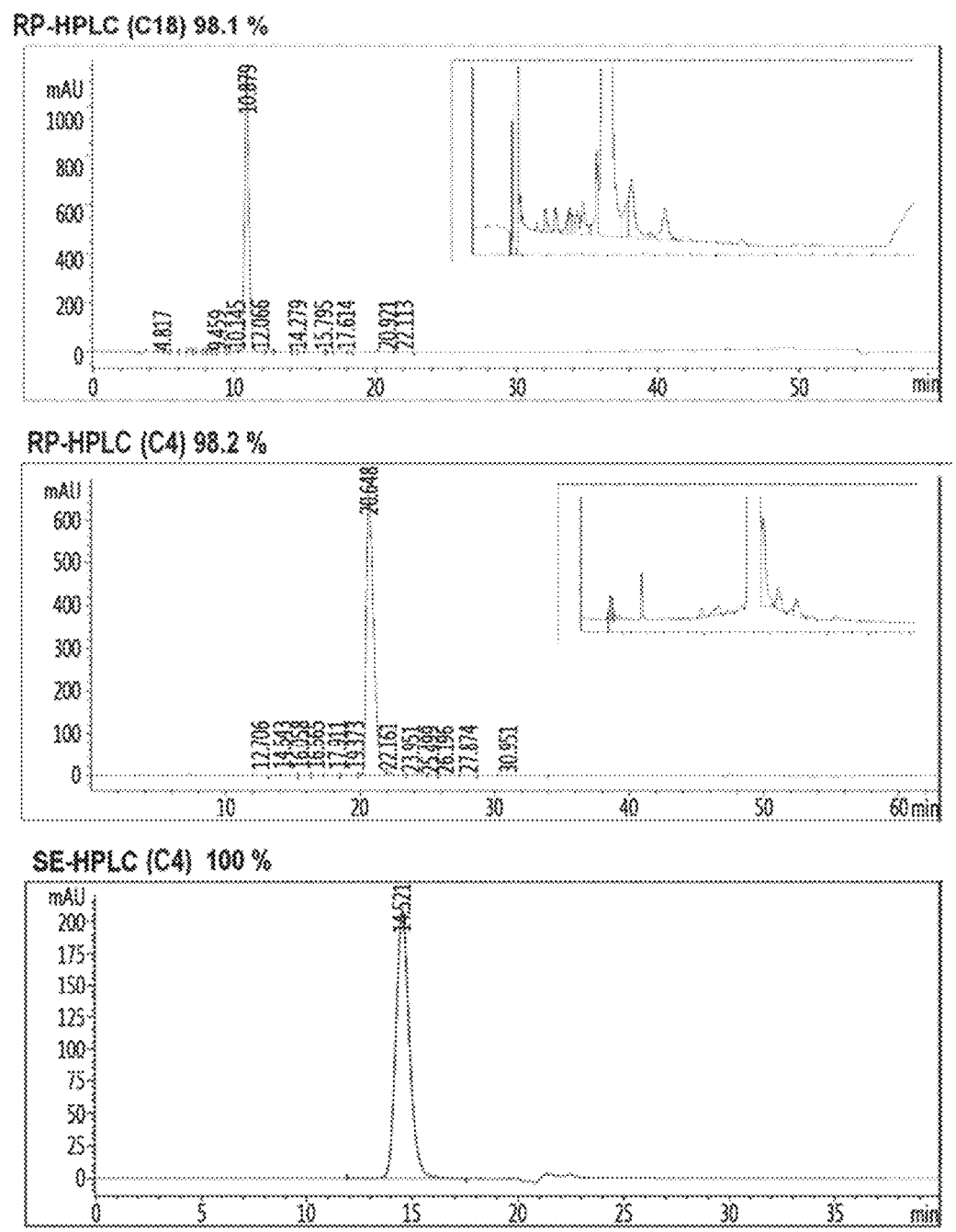

[Figure 2c]
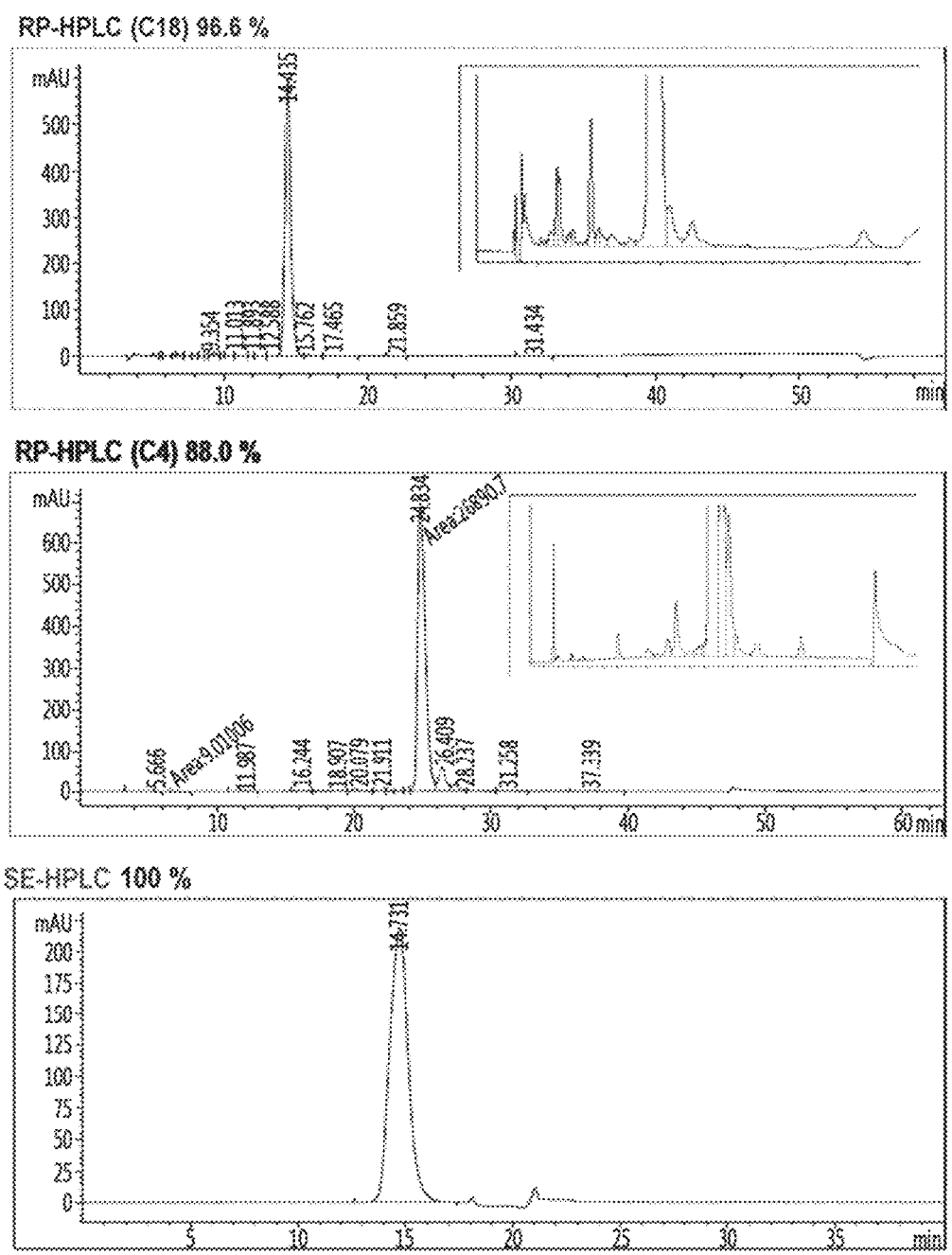

[Figure 2d]
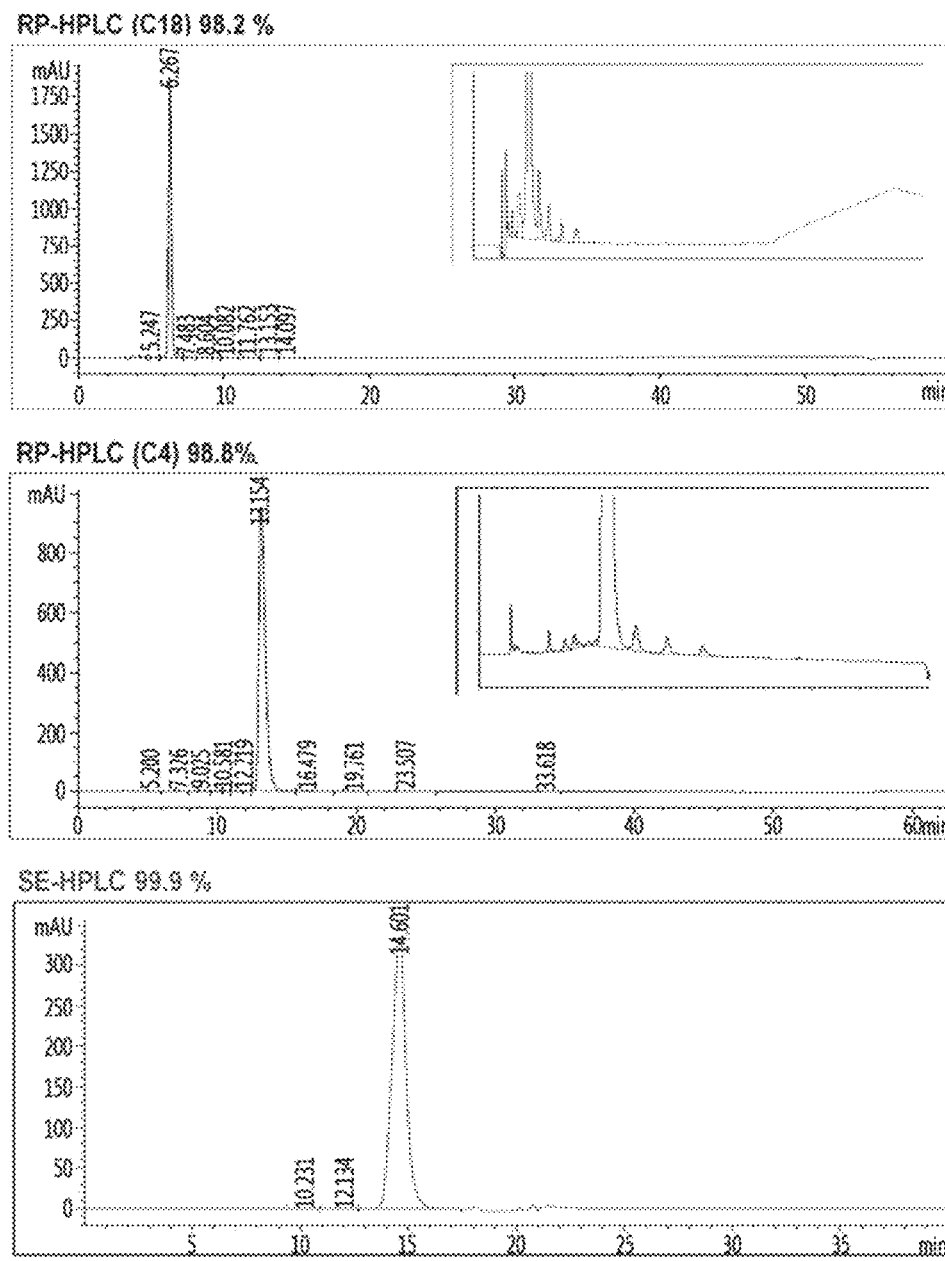

[Figure 3a]
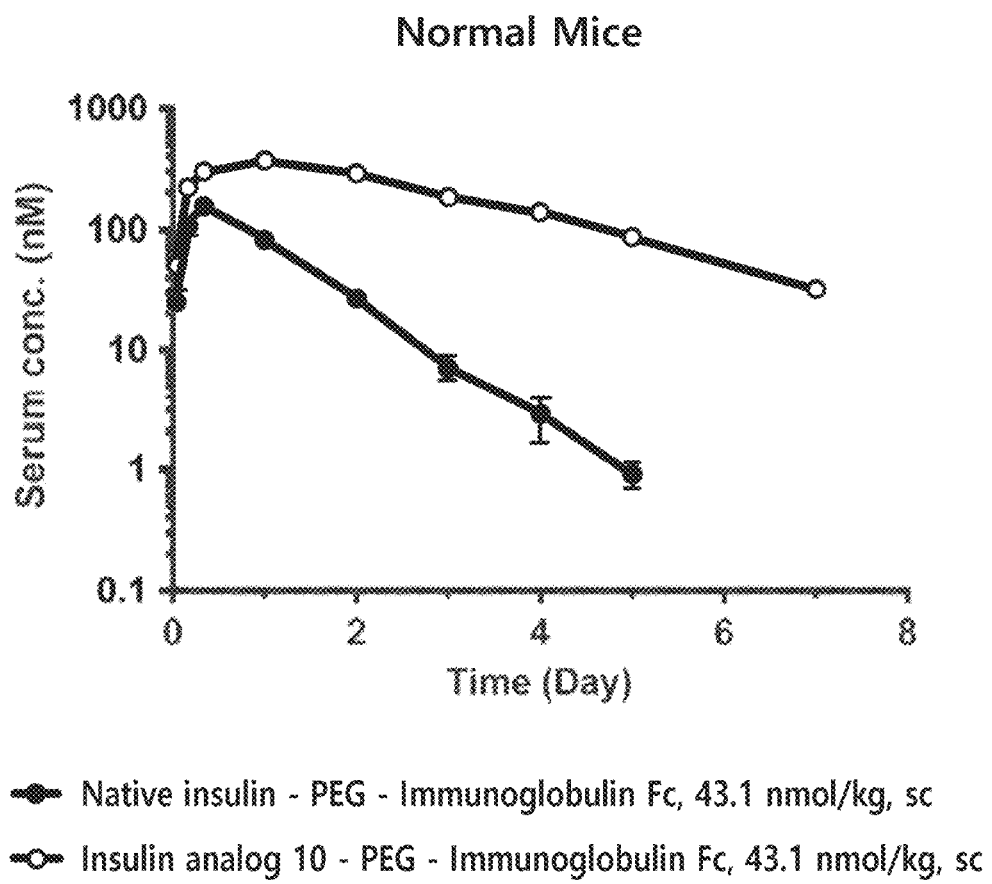

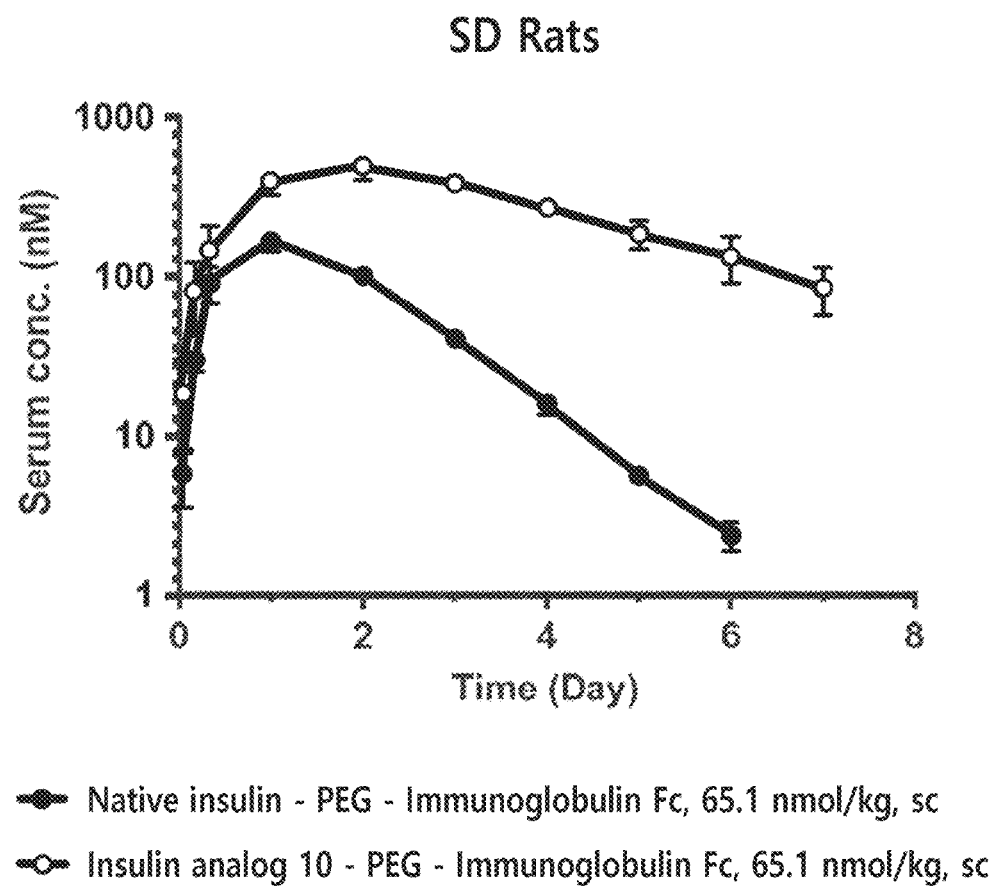
[Figure 3b]

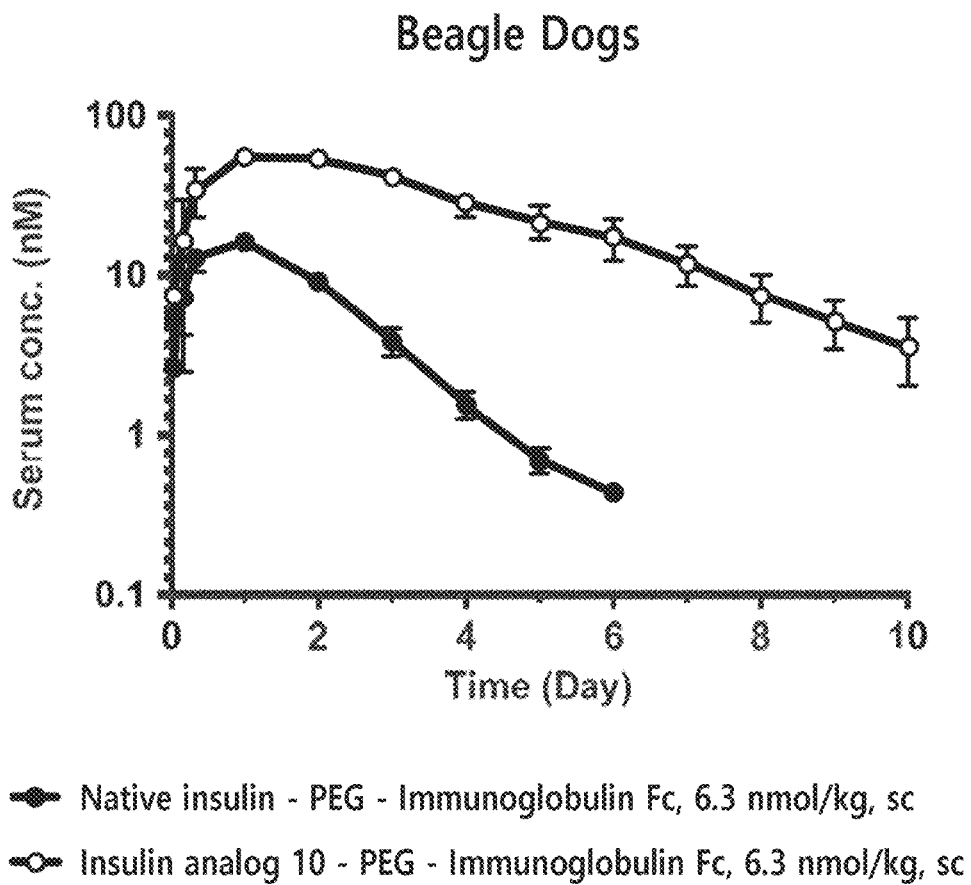
[Figure 3c]

[Figure 4]
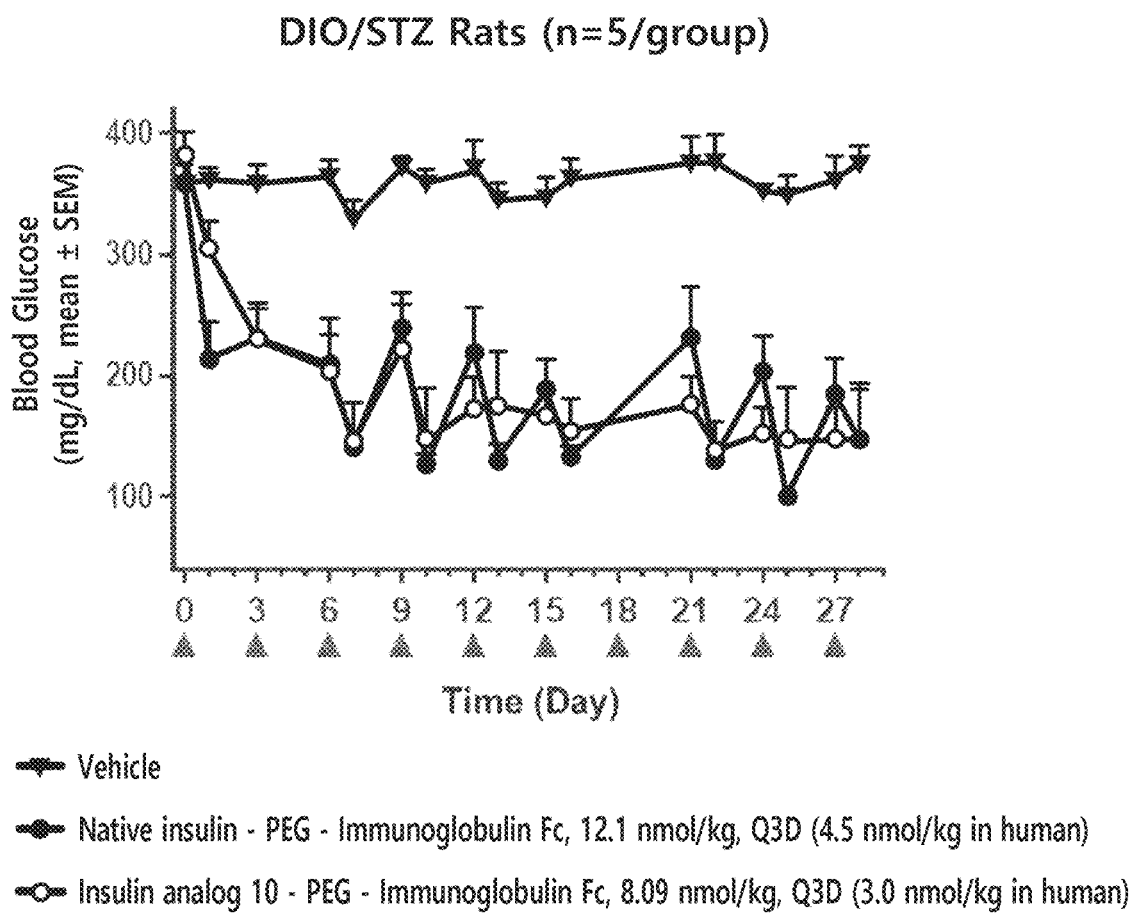

SEQUENCE LISTING

```
<160> NUMBER OF SEQ ID NOS: 58

<210> SEQ ID NO 1
<211> LENGTH: 34
<212> TYPE: DNA
<213> ORGANISM: Artificial Sequence
<220> FEATURE:
<223> OTHER INFORMATION: Primer

<400> SEQUENCE: 1
cagcatctgc tccctccatc agctggagaa ctac                              34

<210> SEQ ID NO 2
<211> LENGTH: 34
<212> TYPE: DNA
<213> ORGANISM: Artificial Sequence
<220> FEATURE:
<223> OTHER INFORMATION: Primer

<400> SEQUENCE: 2
gtagttctcc agctgatgga gggagcagat gctg                              34

<210> SEQ ID NO 3
<211> LENGTH: 34
<212> TYPE: DNA
<213> ORGANISM: Artificial Sequence
<220> FEATURE:
```

<223> OTHER INFORMATION: Primer

<400> SEQUENCE: 3
cagcatctgc tccctcaagc agctggagaa ctac                                      34

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
gtagttctcc agctgcttga gggagcagat gctg                                      34

<210> SEQ ID NO 5
<211> LENGTH: 34
<212> TYPE: DNA
<213> ORGANISM: Artificial Sequence
<220> FEATURE:
<223> OTHER INFORMATION: Primer

<400> SEQUENCE: 5
ctaccagctg gagaacgagt gcaactgagg atcc                                      34

<210> SEQ ID NO 6
<211> LENGTH: 34
<212> TYPE: DNA
<213> ORGANISM: Artificial Sequence
<220> FEATURE:
<223> OTHER INFORMATION: Primer

<400> SEQUENCE: 6
ggatcctcag ttgcactcgt tctccagctg gtag                                      34

<210> SEQ ID NO 7
<211> LENGTH: 34
<212> TYPE: DNA
<213> ORGANISM: Artificial Sequence
<220> FEATURE:
<223> OTHER INFORMATION: Primer

<400> SEQUENCE: 7
ctaccagctg gagaactcct gcaactgagg atcc                                      34

<210> SEQ ID NO 8
<211> LENGTH: 34
<212> TYPE: DNA
<213> ORGANISM: Artificial Sequence
<220> FEATURE:
<223> OTHER INFORMATION: Primer

<400> SEQUENCE: 8
ggatcctcag ttgcaggagt tctccagctg gtag                                      34

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
ctaccagctg gagaacacct gcaactgagg atcc                                      34

```
<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
ggatcctcag ttgcaggtgt tctccagctg gtag                           34

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
ctggtggaag ctctcgagct agtgtgcggg gaac                           34

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
gttccccgca cactagctcg agagcttcca ccag                           34

<210> SEQ ID NO 13
<211> LENGTH: 34
<212> TYPE: DNA
<213> ORGANISM: Artificial Sequence
<220> FEATURE:
<223> OTHER INFORMATION: Primer

<400> SEQUENCE: 13
ctggtggaag ctctctccct agtgtgcggg gaac                           34

<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14
gttccccgca cactagggag agagcttcca ccag                           34

<210> SEQ ID NO 15
<211> LENGTH: 34
<212> TYPE: DNA
<213> ORGANISM: Artificial Sequence
<220> FEATURE:
<223> OTHER INFORMATION: Primer

<400> SEQUENCE: 15
ctggtggaag ctctcaccct agtgtgcggg gaac                           34

<210> SEQ ID NO 16
<211> LENGTH: 34
<212> TYPE: DNA
<213> ORGANISM: Artificial Sequence
<220> FEATURE:
<223> OTHER INFORMATION: Primer
```

-continued

<400> SEQUENCE: 16
gttccccgca cactagggtg agagcttcca ccag  34

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17
cagcatctgc tccctcgccc agctggagaa ctac  34

<210> SEQ ID NO 18
<211> LENGTH: 34
<212> TYPE: DNA
<213> ORGANISM: Artificial Sequence
<220> FEATURE:
<223> OTHER INFORMATION: Primer

<400> SEQUENCE: 18
gtagttctcc agctgggcga gggagcagat gctg  34

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
cagcatctgc tccctcgacc agctggagaa ctac  34

<210> SEQ ID NO 20
<211> LENGTH: 34
<212> TYPE: DNA
<213> ORGANISM: Artificial Sequence
<220> FEATURE:
<223> OTHER INFORMATION: Primer

<400> SEQUENCE: 20
gtagttctcc agctggtcga gggagcagat gctg  34

<210> SEQ ID NO 21
<211> LENGTH: 34
<212> TYPE: DNA
<213> ORGANISM: Artificial Sequence
<220> FEATURE:
<223> OTHER INFORMATION: Primer

<400> SEQUENCE: 21
ctggtggaag ctctcgacct agtgtgcggg gaac  34

<210> SEQ ID NO 22
<211> LENGTH: 34
<212> TYPE: DNA
<213> ORGANISM: Artificial Sequence
<220> FEATURE:
<223> OTHER INFORMATION: Primer

<400> SEQUENCE: 22
gttccccgca cactaggtcg agagcttcca ccag  34

<210> SEQ ID NO 23
<211> LENGTH: 33

```
<212> TYPE: DNA
<213> ORGANISM: Artificial Sequence
<220> FEATURE:
<223> OTHER INFORMATION: Primer

<400> SEQUENCE: 23
ggggaacgag gcttcgacta cacacccaag acc                                33

<210> SEQ ID NO 24
<211> LENGTH: 33
<212> TYPE: DNA
<213> ORGANISM: Artificial Sequence
<220> FEATURE:
<223> OTHER INFORMATION: Primer

<400> SEQUENCE: 24
ggtcttgggt gtgtagtcga agcctcgttc ccc                                33

<210> SEQ ID NO 25
<211> LENGTH: 33
<212> TYPE: DNA
<213> ORGANISM: Artificial Sequence
<220> FEATURE:
<223> OTHER INFORMATION: Primer

<400> SEQUENCE: 25
ggggaacgag gcttcgagta cacacccaag acc                                33

<210> SEQ ID NO 26
<211> LENGTH: 33
<212> TYPE: DNA
<213> ORGANISM: Artificial Sequence
<220> FEATURE:
<223> OTHER INFORMATION: Primer

<400> SEQUENCE: 26
ggtcttgggt gtgtactcga agcctcgttc ccc                                33

<210> SEQ ID NO 27
<211> LENGTH: 258
<212> TYPE: DNA
<213> ORGANISM: Artificial Sequence
<220> FEATURE:
<223> OTHER INFORMATION: Analog 1

<400> SEQUENCE: 27
ttcgttaacc aacacttgtg tggctcacac ctggtggaag ctctctacct agtgtgcggg   60
gaacgaggct tcttctacac acccaagacc cgccggagg cagaggacct gcaggtgggg   120
caggtggagc tgggcggggg ccctggtgca ggcagcctgc agcccttggc cctggagggg   180
tccctgcaga agcgtggcat tgtggaacaa tgctgtacca gcatctgctc cctccatcag   240
ctggagaact actgcaac                                                258

<210> SEQ ID NO 28
<211> LENGTH: 86
<212> TYPE: PRT
<213> ORGANISM: Artificial Sequence
<220> FEATURE:
<223> OTHER INFORMATION: Analog 1

<400> SEQUENCE: 28

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
```

```
                20                  25                  30
Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu His Gln
65                  70                  75                  80

Leu Glu Asn Tyr Cys Asn
                85

<210> SEQ ID NO 29
<211> LENGTH: 258
<212> TYPE: DNA
<213> ORGANISM: Artificial Sequence
<220> FEATURE:
<223> OTHER INFORMATION: Analog 2

<400> SEQUENCE: 29
ttcgttaacc aacacttgtg tggctcacac ctggtggaag ctctctacct agtgtgcggg      60
gaacgaggct tcttctacac acccaagacc cgccggagg cagaggacct gcaggtgggg     120
caggtggagc tgggcggggg ccctggtgca ggcagcctgc agcccttggc cctggagggg    180
tccctgcaga agcgtggcat tgtggaacaa tgctgtacca gcatctgctc cctcaagcag    240
ctggagaact actgcaac                                                  258

<210> SEQ ID NO 30
<211> LENGTH: 86
<212> TYPE: PRT
<213> ORGANISM: Artificial Sequence
<220> FEATURE:
<223> OTHER INFORMATION: Analog 2

<400> SEQUENCE: 30

Phe Val Asn Gln His Leu Cys Gly Ser His Leu Val Glu Ala Leu Tyr
1               5                  10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Lys Gln
65                  70                  75                  80

Leu Glu Asn Tyr Cys Asn
                85

<210> SEQ ID NO 31
<211> LENGTH: 258
<212> TYPE: DNA
<213> ORGANISM: Artificial Sequence
<220> FEATURE:
<223> OTHER INFORMATION: Analog 3

<400> SEQUENCE: 31
ttcgttaacc aacacttgtg tggctcacac ctggtggaag ctctctacct agtgtgcggg      60
gaacgaggct tcttctacac acccaagacc cgccggagg cagaggacct gcaggtgggg     120
caggtggagc tgggcggggg ccctggtgca ggcagcctgc agcccttggc cctggagggg    180
tccctgcaga agcgtggcat tgtggaacaa tgctgtacca gcatctgctc cctctaccag    240
```

-continued

```
ctggagaacg agtgcaac                                                    258
```

<210> SEQ ID NO 32
<211> LENGTH: 86
<212> TYPE: PRT
<213> ORGANISM: Artificial Sequence
<220> FEATURE:
<223> OTHER INFORMATION: Analog 3

<400> SEQUENCE: 32

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Glu Cys Asn
                85
```

<210> SEQ ID NO 33
<211> LENGTH: 258
<212> TYPE: DNA
<213> ORGANISM: Artificial Sequence
<220> FEATURE:
<223> OTHER INFORMATION: Analog 4

<400> SEQUENCE: 33

```
ttcgttaacc aacacttgtg tggctcacac ctggtggaag ctctctacct agtgtgcggg      60
gaacgaggct tcttctacac acccaagacc cgccggagg cagaggacct gcaggtgggg     120
caggtggagc tgggcggggg ccctggtgca ggcagcctgc agcccttggc cctggagggg    180
tccctgcaga gcgtggcat tgtggaacaa tgctgtacca gcatctgctc cctctaccag    240
ctggagaact cctgcaac                                                   258
```

<210> SEQ ID NO 34
<211> LENGTH: 86
<212> TYPE: PRT
<213> ORGANISM: Artificial Sequence
<220> FEATURE:
<223> OTHER INFORMATION: Analog 4

<400> SEQUENCE: 34

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Ser Cys Asn
                85
```

<210> SEQ ID NO 35
<211> LENGTH: 258
<212> TYPE: DNA
<213> ORGANISM: Artificial Sequence
<220> FEATURE:
<223> OTHER INFORMATION: Analog 5

<400> SEQUENCE: 35

```
ttcgttaacc aacacttgtg tggctcacac ctggtggaag ctctctacct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctctaccag     240
ctggagaaca cctgcaac                                                   258
```

<210> SEQ ID NO 36
<211> LENGTH: 86
<212> TYPE: PRT
<213> ORGANISM: Artificial Sequence
<220> FEATURE:
<223> OTHER INFORMATION: Analog 5

<400> SEQUENCE: 36

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Thr Cys Asn
            85

<210> SEQ ID NO 37
<211> LENGTH: 258
<212> TYPE: DNA
<213> ORGANISM: Artificial Sequence
<220> FEATURE:
<223> OTHER INFORMATION: Analog 6

<400> SEQUENCE: 37

```
ttcgttaacc aacacttgtg tggctcacac ctggtggaag ctctcgagct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctctaccag     240
ctggagaact actgcaac                                                   258
```

<210> SEQ ID NO 38
<211> LENGTH: 86
<212> TYPE: PRT
<213> ORGANISM: Artificial Sequence
<220> FEATURE:
<223> OTHER INFORMATION: Analog 6

<400> SEQUENCE: 38

Phe Val Asn Gln His Leu Cys Gly Ser His Leu Val Glu Ala Leu Glu

```
1               5                   10                  15
Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85
```

<210> SEQ ID NO 39
<211> LENGTH: 258
<212> TYPE: DNA
<213> ORGANISM: Artificial Sequence
<220> FEATURE:
<223> OTHER INFORMATION: Analog 7

<400> SEQUENCE: 39

```
ttcgttaacc aacacttgtg tggctcacac ctggtggaag ctctctccct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga gcgtggcat tgtggaacaa tgctgtacca gcatctgctc cctctaccag     240
ctggagaact actgcaac                                                   258
```

<210> SEQ ID NO 40
<211> LENGTH: 86
<212> TYPE: PRT
<213> ORGANISM: Artificial Sequence
<220> FEATURE:
<223> OTHER INFORMATION: Analog 7

<400> SEQUENCE: 40

```
Phe Val Asn Gln His Leu Cys Gly Ser His Leu Val Glu Ala Leu Ser
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85
```

<210> SEQ ID NO 41
<211> LENGTH: 258
<212> TYPE: DNA
<213> ORGANISM: Artificial Sequence
<220> FEATURE:
<223> OTHER INFORMATION: Analog 8

<400> SEQUENCE: 41

```
ttcgttaacc aacacttgtg tggctcacac ctggtggaag ctctcaccct agtgtgcggg      60
gaacgaggct tcttctacac acccaagacc cgccgggagg cagaggacct gcaggtgggg     120
```

```
caggtggagc tgggcggggg ccctggtgca ggcagcctgc agcccttggc cctggagggg      180
tccctgcaga agcgtggcat tgtggaacaa tgctgtacca gcatctgctc cctctaccag      240
ctggagaact actgcaac                                                    258
```

<210> SEQ ID NO 42
<211> LENGTH: 86
<212> TYPE: PRT
<213> ORGANISM: Artificial Sequence
<220> FEATURE:
<223> OTHER INFORMATION: Analog 8

<400> SEQUENCE: 42

```
Phe Val Asn Gln His Leu Cys Gly Ser His Leu Val Glu Ala Leu Thr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85
```

<210> SEQ ID NO 43
<211> LENGTH: 258
<212> TYPE: DNA
<213> ORGANISM: Artificial Sequence
<220> FEATURE:
<223> OTHER INFORMATION: Analog 9

<400> SEQUENCE: 43

```
ttcgttaacc aacacttgtg tggctcacac ctggtggaag ctctctacct agtgtgcggg      60
gaacgaggct tcttctacac acccaagacc cgccgggagg cagaggacct gcaggtgggg      120
caggtggagc tgggcggggg ccctggtgca ggcagcctgc agcccttggc cctggagggg      180
tccctgcaga agcgtggcat tgtggaacaa tgctgtacca gcatctgctc cctcgcccag      240
ctggagaact actgcaac                                                    258
```

<210> SEQ ID NO 44
<211> LENGTH: 86
<212> TYPE: PRT
<213> ORGANISM: Artificial Sequence
<220> FEATURE:
<223> OTHER INFORMATION: Analog 9

<400> SEQUENCE: 44

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Ala Gln
65                  70                  75                  80
```

<210> SEQ ID NO 45
<211> LENGTH: 258
<212> TYPE: DNA
<213> ORGANISM: Artificial Sequence
<220> FEATURE:
<223> OTHER INFORMATION: Analog 10

<400> SEQUENCE: 45

```
ttcgttaacc aacacttgtg tggctcacac ctggtggaag ctctctacct agtgtgcggg      60
gaacgaggct tcttctacac acccaagacc cgccggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctcgaccag     240
ctggagaact actgcaac                                                  258
```

<210> SEQ ID NO 46
<211> LENGTH: 86
<212> TYPE: PRT
<213> ORGANISM: Artificial Sequence
<220> FEATURE:
<223> OTHER INFORMATION: Analog 10

<400> SEQUENCE: 46

Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys Thr Arg Arg
            20                  25                  30
Glu Ala Glu Asp Leu Gln Val Gly Gln Val Glu Leu Gly Gly Gly Pro
        35                  40                  45
Gly Ala Gly Ser Leu Gln Pro Leu Ala Leu Glu Gly Ser Leu Gln Lys
    50                  55                  60
Arg Gly Ile Val Glu Gln Cys Cys Thr Ser Ile Cys Ser Leu Asp Gln
65                  70                  75                  80
Leu Glu Asn Tyr Cys Asn
            85

<210> SEQ ID NO 47
<211> LENGTH: 258
<212> TYPE: DNA
<213> ORGANISM: Artificial Sequence
<220> FEATURE:
<223> OTHER INFORMATION: Analog 11

<400> SEQUENCE: 47

```
ttcgttaacc aacacttgtg tggctcacac ctggtggaag ctctcgacct agtgtgcggg      60
gaacgaggct tcttctacac acccaagacc cgccggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctctaccag     240
ctggagaact actgcaac                                                  258
```

<210> SEQ ID NO 48
<211> LENGTH: 86
<212> TYPE: PRT
<213> ORGANISM: Artificial Sequence
<220> FEATURE:
<223> OTHER INFORMATION: Analog 11

<400> SEQUENCE: 48

Phe Val Asn Gln His Leu Cys Gly Ser His Leu Val Glu Ala Leu Asp
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 49
<211> LENGTH: 258
<212> TYPE: DNA
<213> ORGANISM: Artificial Sequence
<220> FEATURE:
<223> OTHER INFORMATION: Analog 12

<400> SEQUENCE: 49
ttcgttaacc aaacacttgtg tggctcacac ctggtggaag ctctctacct agtgtgcggg      60
gaacgaggct tcgactacac acccaagacc cgccggagg cagaggacct gcaggtgggg     120
caggtggagc tgggcggggg ccctggtgca ggcagcctgc agcccttggc cctggagggg    180
tccctgcaga agcgtggcat tgtgaacaa tgctgtacca gcatctgctc cctctaccag     240
ctggagaact actgcaac                                                  258

<210> SEQ ID NO 50
<211> LENGTH: 86
<212> TYPE: PRT
<213> ORGANISM: Artificial Sequence
<220> FEATURE:
<223> OTHER INFORMATION: Analog 12

<400> SEQUENCE: 50

Phe Val Asn Gln His Leu Cys Gly Ser His Leu Val Glu Ala Leu Tyr
1               5                   10                  15

Leu Val Cys Gly Glu Arg Gly Phe Asp Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 51
<211> LENGTH: 258
<212> TYPE: DNA
<213> ORGANISM: Artificial Sequence
<220> FEATURE:
<223> OTHER INFORMATION: Analog 13

<400> SEQUENCE: 51
ttcgttaacc aaacacttgtg tggctcacac ctggtggaag ctctctacct agtgtgcggg      60

```
gaacgaggct tcgagtacac acccaagacc cgccgggagg cagaggacct gcaggtgggg    120
caggtggagc tgggcggggg ccctggtgca ggcagcctgc agcccttggc cctggagggg    180
tccctgcaga agcgtggcat tgtggaacaa tgctgtacca gcatctgctc cctctaccag    240
ctggagaact actgcaac                                                   258

<210> SEQ ID NO 52
<211> LENGTH: 86
<212> TYPE: PRT
<213> ORGANISM: Artificial Sequence
<220> FEATURE:
<223> OTHER INFORMATION: Analog 13

<400> SEQUENCE: 52

Phe Val Asn Gln His Leu Cys Gly Ser His Leu Val Glu Ala Leu Tyr
1               5                   10                  15

Leu Val Cys Gly Glu Arg Gly Phe Glu Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 53
<211> LENGTH: 21
<212> TYPE: PRT
<213> ORGANISM: Homo sapiens

<400> SEQUENCE: 53

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 54
<211> LENGTH: 30
<212> TYPE: PRT
<213> ORGANISM: Homo sapiens

<400> SEQUENCE: 54

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 55
<211> LENGTH: 21
<212> TYPE: PRT
<213> ORGANISM: Artificial Sequence
<220> FEATURE:
<223> OTHER INFORMATION: Insulin analog, A-chain
<220> FEATURE:
<221> NAME/KEY: MISC_FEATURE
<222> LOCATION: (1)
<223> OTHER INFORMATION: Xaa is alanine, glycine, glutamine, histidine,
      glutamic acid, or asparagine
<220> FEATURE:
<221> NAME/KEY: MISC_FEATURE
```

```
<222> LOCATION: (5)
<223> OTHER INFORMATION: Xaa is alanine, glutamic acid, glutamine,
      histidine, or asparagine
<220> FEATURE:
<221> NAME/KEY: MISC_FEATURE
<222> LOCATION: (12)
<223> OTHER INFORMATION: Xaa is alanine, serine, glutamine, glutamic
      acid, histidine, or asparagine
<220> FEATURE:
<221> NAME/KEY: MISC_FEATURE
<222> LOCATION: (14)
<223> OTHER INFORMATION: Xaa is tyrosine, histidine, lysine, alanine, or
      aspartic acid
<220> FEATURE:
<221> NAME/KEY: MISC_FEATURE
<222> LOCATION: (16)
<223> OTHER INFORMATION: Xaa is alanine, leucine, tyrosine, histidine,
      glutamic acid, or asparagine
<220> FEATURE:
<221> NAME/KEY: MISC_FEATURE
<222> LOCATION: (19)
<223> OTHER INFORMATION: Xaa is tyrosine, glutamic acid, serine, or
      threonine
<220> FEATURE:
<221> NAME/KEY: MISC_FEATURE
<222> LOCATION: (21)
<223> OTHER INFORMATION: Xaa is asparagine, glycine, histidine, or
      alanine

<400> SEQUENCE: 55

Xaa Ile Val Glu Xaa Cys Cys Thr Ser Ile Cys Xaa Leu Xaa Gln Xaa
1               5                   10                  15

Glu Asn Xaa Cys Xaa
            20

<210> SEQ ID NO 56
<211> LENGTH: 30
<212> TYPE: PRT
<213> ORGANISM: Artificial Sequence
<220> FEATURE:
<223> OTHER INFORMATION: Insulin analog, B-chain
<220> FEATURE:
<221> NAME/KEY: MISC_FEATURE
<222> LOCATION: (16)
<223> OTHER INFORMATION: Xaa is tyrosine, glutamic acid, serine,
      threonine, or aspartic acid
<220> FEATURE:
<221> NAME/KEY: MISC_FEATURE
<222> LOCATION: (25)
<223> OTHER INFORMATION: Xaa is phenylalanine, aspartic acid, or
      glutamic acid
<220> FEATURE:
<221> NAME/KEY: MISC_FEATURE
<222> LOCATION: (27)
<223> OTHER INFORMATION: Xaa is threonine, or is absent
<220> FEATURE:
<221> NAME/KEY: MISC_FEATURE
<222> LOCATION: (28)
<223> OTHER INFORMATION: Xaa is proline, glutamic acid, or aspartic
      acid, or is absent

<400> SEQUENCE: 56

Phe Val Asn Gln His Leu Cys Gly Ser His Leu Val Glu Ala Leu Xaa
1               5                   10                  15

Leu Val Cys Gly Glu Arg Gly Phe Xaa Tyr Xaa Xaa Lys Thr
            20                  25                  30

<210> SEQ ID NO 57
<211> LENGTH: 4
<212> TYPE: PRT
<213> ORGANISM: Artificial Sequence
<220> FEATURE:
<223> OTHER INFORMATION: Linker
```

```
<400> SEQUENCE: 57

Gly Gly Gly Ser
1

<210> SEQ ID NO 58
<211> LENGTH: 5
<212> TYPE: PRT
<213> ORGANISM: Artificial Sequence
<220> FEATURE:
<223> OTHER INFORMATION: Linker

<400> SEQUENCE: 58

Gly Gly Gly Gly Ser
1               5
```

INSULIN ANALOG COMPLEX WITH REDUCED AFFINITY FOR INSULIN RECEPTOR AND USE THEREOF

CROSS REFERENCE TO RELATED APPLICATIONS

This application is a National Stage of International Application No. PCT/KR2018/003489 filed Mar. 23, 2018, claiming priority based on Korean Patent Application No. 10-2017-0037101 filed Mar. 23, 2017.

SEQUENCE LISTING

The content of the electronically submitted sequence listing, file name: Sequence_Listing_As_Filed.txt; size: 25,242 bytes; and date of creation: Jul. 15, 2021, filed herewith, is incorporated herein by reference in its entirety.

TECHNICAL FIELD

The present invention relates to a conjugate of an insulin analog and a use thereof.

BACKGROUND ART

It is known that proteins in the body are removed by various routes including decomposition by proteases in the blood, excretion through the kidney, removal by receptors, etc. In this regard, various attempts have been made to improve therapeutic effects of proteins via increase of the half-life of physiological proteins by avoiding protein clearance mechanisms.

Generally, insulin is a hormone secreted by the pancreas of the human body which regulates blood glucose levels and has the role of maintaining normal blood glucose levels while carrying excess glucose in the blood to cells to provide energy for cells. In diabetic patients, however, insulin does not function properly due to lack of insulin, resistance to insulin, and loss of beta-cell function. As a result, diabetic patients cannot utilize the blood glucose as an energy source, but show symptoms of hyperglycemia with a high blood glucose level and excrete the glucose in the urine, which becomes the cause of various complications. Accordingly, insulin therapy is essential for patients with abnormal insulin production (type I) or insulin resistance (type II), and blood glucose levels can be normally regulated by insulin administration.

However, like other protein and peptide hormones, insulin has a very short in vivo half-life, and thus does not exhibit a continuous therapeutic effect. Therefore, in order to exert its effect, insulin is required to be repeatedly administered. Such frequent administration causes severe pain and discomfort for the patients, and thus there is a need to improve the administration from the aspects of patient compliance, safety, and convenience.

Accordingly, studies have focused on the development of various protein formulations, chemical conjugates (e.g., fatty acid conjugate), etc. for improving the therapeutic effects as well as the quality of patients' lives by reducing the frequency of administration through the increase of the in vivo half-life of these protein drugs such as insulin.

According to a previous report, 50% or more of insulin is removed in the kidneys and the rest is removed via a receptor mediated clearance (RMC) process in target sites such as muscle, fat, liver, etc.

In this regard, there were reports (*J Pharmacol Exp Ther* (1998) 286: 959. Diabetes Care (1990) 13: 923, and *Diabetes* (1990) 39: 1033, etc.) that in vitro activity is reduced to avoid RMC of insulin, thereby increasing the insulin level in the blood. However, in *J Pharmacol Exp Ther* (1998) 286: 959, *Diabetes Care* (1990) 13: 923, the insulin analogs suggested had substitutions of at least two amino acids or no specific result was provided, whereas in *Diabetes* (1990) 39: 1033, the insulin analogs showed no change in their binding affinity to receptors or their activities were reduced by substituting the amino acids which were directly involved in binding to insulin receptors. That is, there is still a need for the development of insulin analogs with increased duration.

DISCLOSURE

Technical Problem

An object of the present invention is to provide a conjugate of an insulin analog.

Another object of the present invention is to provide a polynucleotide encoding the conjugate; a vector including the polynucleotide; and a transformant including the polynucleotide or the vector including the polynucleotide.

Still another object of the present invention is to provide a method for preparing the conjugate.

Still another object of the present invention is to provide a composition, e.g., a pharmaceutical composition, including the conjugate of the insulin analog.

Still another object of the present invention is to provide a long-acting formulation with increased in vivo duration and/or stability compared to the conjugate of native insulin, including the conjugate of the insulin analog.

Still another object of the present invention is to provide a pharmaceutical composition for preventing or treating an insulin-related disease, e.g., diabetes, which comprises the conjugate of the insulin analog.

Still another object of the present invention is to provide a method for treating an insulin-related disease, e.g., diabetes, which includes a step of administering the conjugate of the insulin analog or the composition thereof to a subject in need thereof.

Still another object of the present invention is to provide a use of the conjugate of the insulin analog in the preparation of a medicament.

Still another object of the present invention is to provide a use of the conjugate of the insulin analog in the treatment of an insulin-related disease, specifically diabetes.

Technical Solution

In order to achieve the above objects, an aspect of the present invention provides an insulin analog conjugate.

More specifically, an aspect of the present invention provides a conjugate represented by the following Formula 1:

$$X\text{-}L_a\text{-}F \qquad \text{[Formula 1]}$$

wherein in Formula 1,

X is an insulin analog comprising a modification of one or more amino acids selected from the group consisting of the 16$^{th}$ amino acid of the B-chain, the 25$^{th}$ amino acid of the B-chain, the 14$^{th}$ amino acid of the A-chain, and the 19$^{th}$ amino acid of the A-chain of native insulin;

L is a linker;

a is 0 or a natural number, with the proviso that when a is 2 or greater, each L is independent from each other; and F is a substance capable of increasing the half-life of X.

In an exemplary embodiment, X comprises one or more modifications selected from the group consisting of a modification of the 16$^{th}$ amino acid of the B-chain of native insulin, tyrosine, into glutamic acid, serine, threonine, or aspartic acid; a modification of the 25$^{th}$ amino acid of the B-chain of native insulin, phenylalanine, into aspartic acid or glutamic acid; a modification of the 14$^{th}$ amino acid of the A-chain of native insulin, tyrosine, into histidine, lysine, alanine, or aspartic acid; and a modification of the 19$^{th}$ amino acid of the A-chain of native insulin, tyrosine, into glutamic acid, serine, or threonine.

In another exemplary embodiment, X is an insulin analog comprising all combinations of an A-chain of SEQ ID NO: 55 indicated in General Formula 2 and a B-chain of SEQ ID NO: 56 indicated in General Formula 3 (with the proviso that native insulin is excluded; that is, the peptide where the A-chain coincides with SEQ ID NO: 53 while the B-chain also coincides with SEQ ID NO: 54 is excluded):

[General Formula 2]
(SEQ ID NO: 55)
Xaa1-Ile-Val-Glu-Xaa5-Cys-Cys-Thr-Ser-Ile-Cys-Xaa12-Leu-Xaa14-Gln-Xaa16-Glu-Asn-Xaa19-Cys-Xaa21 wherein in General Formula 2,

Xaa1 is alanine, glycine, glutamine, histidine, glutamic acid, or asparagine;

Xaa5 is alanine, glutamic acid, glutamine, histidine, or asparagine;

Xaa12 is alanine, serine, glutamine, glutamic acid, histidine, or asparagine;

Xaa14 is tyrosine, histidine, lysine, alanine, or aspartic acid;

Xaa16 is alanine, leucine, tyrosine, histidine, glutamic acid, or asparagine;

Xaa19 is tyrosine, glutamic acid, serine, or threonine; and

Xaa21 is asparagine, glycine, histidine, or alanine; and

[General Formula 3]
(SEQ ID NO: 56)
Phe-Val-Asn-Gln-His-Leu-Cys-Gly-Ser-His-Leu-Val-Gln-Ala-Leu-Xaa16-Leu-Val-Cys-Gly-Glu-Arg-Gly-Phe-Xaa25-Tyr-Xaa27-Xaa28-Lys-Thr wherein in General Formula 3, Xaa16 is tyrosine, glutamic acid, serine, threonine, or aspartic acid;

Xaa25 is phenylalanine, aspartic acid, or glutamic acid;

Xaa27 is threonine or is absent; and

Xaa28 is proline, glutamic acid, or aspartic acid, or is absent.

In still another exemplary embodiment, X comprises an A-chain of SEQ ID NO: 55 indicated in General Formula 2 and a B-chain of SEQ ID NO: 54.

In still another exemplary embodiment, X comprises an A-chain of SEQ ID NO: 53 and a B-chain of SEQ ID NO: 56 indicated in General Formula 3.

In still another exemplary embodiment, in General Formula 2,

Xaa1 is glycine, Xaa5 is glutamine, Xaa12 is serine, Xaa14 is tyrosine, histidine, lysine, alanine, or aspartic acid, Xaa16 is leucine, Xaa19 is tyrosine, glutamic acid, serine, or threonine, and Xaa21 is asparagine; and in General Formula 3, Xaa16 is tyrosine, glutamic acid, serine, threonine, or aspartic acid, Xaa25 is phenylalanine, aspartic acid, or glutamic acid, Xaa27 is threonine, and Xaa28 is proline.

In still another exemplary embodiment, in General Formula 2,

Xaa1 is glycine, Xaa5 is glutamine, Xaa12 is serine, Xaa14 is tyrosine, Xaa16 is leucine, Xaa19 is tyrosine, glutamic acid, or serine, and Xaa21 is asparagine; and in General Formula 3, Xaa16 is tyrosine, glutamic acid, serine, or aspartic acid, Xaa25 is phenylalanine, aspartic acid, or glutamic acid, Xaa27 is threonine, and Xaa28 is proline.

In still another exemplary embodiment, X is characterized in that:

(1) in General Formula 2, Xaa1 is glycine, Xaa5 is glutamine, Xaa12 is serine, Xaa14 is histidine, Xaa16 is leucine, Xaa19 is tyrosine, and Xaa21 is asparagine; and in General Formula 3, Xaa16 is tyrosine, Xaa25 is phenylalanine, Xaa27 is threonine, and Xaa28 is proline;

(2) in General Formula 2, Xaa1 is glycine, Xaa5 is glutamine, Xaa12 is serine, Xaa14 is lysine, Xaa16 is leucine, Xaa19 is tyrosine, and Xaa21 is asparagine; and in General Formula 3, Xaa16 is tyrosine, Xaa25 is phenylalanine, Xaa27 is threonine, and Xaa28 is proline;

(3) in General Formula 2, Xaa1 is glycine, Xaa5 is glutamine, Xaa12 is serine, Xaa1.4 is tyrosine, Xaa16 is leucine, Xaa19 is glutamic acid, and Xaa21 is asparagine; and in General Formula 3, Xaa16 is tyrosine, Xaa25 is phenylalanine, Xaa27 is threonine, and Xaa28 is proline;

(4) in General Formula 2, Xaa1 is glycine, Xaa5 is glutamine, Xaa12 is serine, Xaa14 is tyrosine, Xaa16 is leucine, Xaa19 is serine, and Xaa21 is asparagine; and in General Formula 3, Xaa16 is tyrosine, Xaa25 is phenylalanine, Xaa27 is threonine, and Xaa28 is proline;

(5) in General Formula 2, Xaa1 is glycine, Xaa5 is glutamine, Xaa12 is serine, Xaa14 is tyrosine, Xaa16 is leucine, Xaa19 is threonine, and Xaa21 is asparagine; and in General Formula 3, Xaa16 is tyrosine, Xaa25 is phenylalanine, Xaa27 is threonine, and Xaa28 is proline;

(6) in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is glutamic acid, Xaa25 is phenylalanine, Xaa27 is threonine, and Xaa28 is proline;

(7) in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is serine, Xaa25 is phenylalanine, Xaa27 is threonine, and Xaa28 is proline;

(8) in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is threonine, Xaa25 is phenylalanine, Xaa27 is threonine, and Xaa28 is proline;

(9) in General Formula 2, Xaa1 is glycine, Xaa5 is glutamine, Xaa12 is serine, Xaa14 is alanine, Xaa16 is leucine, Xaa19 is tyrosine, and Xaa21 is asparagine; and in General Formula 3, Xaa16 is tyrosine. Xaa25 is phenylalanine, Xaa27 is threonine, and Xaa28 is proline;

(10) in General Formula 2, Xaa1 is glycine, Xaa5 is glutamine, Xaa12 is serine, Xaa14 is aspartic acid, Xaa16 is leucine, Xaa19 is tyrosine, and Xaa21 is asparagine; and in General Formula 3, Xaa16 is tyrosine, Xaa25 is phenylalanine, Xaa27 is threonine, and Xaa28 is proline;

(11) in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is aspartic acid, Xaa25 is phenylalanine, Xaa27 is threonine, and Xaa28 is proline;

(12) in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is tyrosine, Xaa25 is aspartic acid, Xaa27 is threonine, and Xaa28 is proline;

(13) in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is tyrosine, Xaa25 is glutamic acid, Xaa27 is threonine, and Xaa28 is proline.

In still another exemplary embodiment, X is an insulin analog comprising an amino acid sequence selected from the group consisting of SEQ ID NOS: 28, 30, 32, 34, 36, 38, 40, 42, 44, 46, 48, 50, and 52.

In still another exemplary embodiment, in General Formula 2, Xaa1 is glycine, Xaa5 is glutamine, Xaa12 is serine, Xaa14 is tyrosine, Xaa16 is leucine, Xaa19 is glutamic acid, and Xaa21 is asparagine; and in General Formula 3, Xaa16 is tyrosine, Xaa25 is phenylalanine, Xaa27 is threonine, and Xaa28 is proline.

In still another exemplary embodiment, in General Formula 2, Xaa1 is glycine, Xaa5 is glutamine, Xaa12 is serine, Xaa14 is tyrosine, Xaa16 is leucine, Xaa19 is serine, and Xaa21 is asparagine; and in General Formula 3, Xaa16 is tyrosine, Xaa25 is phenylalanine, Xaa27 is threonine, and Xaa28 is proline.

In still another exemplary embodiment, in General Formula 2, Xaa1 is glycine, Xaa5 is glutamine, Xaa12 is serine, Xaa14 is tyrosine, Xaa16 is leucine, Xaa19 is threonine, and Xaa21 is asparagine; and in General Formula 3, Xaa16 is tyrosine, Xaa25 is phenylalanine, Xaa27 is threonine, and Xaa28 is proline.

In still another exemplary embodiment, in General Formula 2, Xaa1 is glycine, Xaa5 is glutamine, Xaa12 is serine, Xaa14 is aspartic acid, Xaa16 is leucine, Xaa19 is tyrosine, and Xaa21 is asparagine, and in General Formula 3, Xaa16 is tyrosine, Xaa25 is phenylalanine, Xaa27 is threonine, and Xaa28 is proline.

In still another exemplary embodiment, in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine, and in General Formula 3, Xaa16 is tyrosine, Xaa25 is aspartic acid, Xaa27 is threonine, and Xaa28 is proline.

In still another exemplary embodiment, in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is tyrosine, Xaa25 is glutamic acid, Xaa27 is threonine, and Xaa28 is proline.

In still another exemplary embodiment, F is selected from the group consisting of a polymer, a fatty acid, a cholesterol, an albumin and a fragment thereof, an albumin-binding material, a polymer of repeating units of a particular amino acid sequence, an antibody, an antibody fragment, an FcRn-binding material, an in vivo connective tissue, a nucleotide, fibronectin, transferrin, saccharide, heparin, and elastin.

In still another exemplary embodiment, the polymer is selected from the group consisting of polyethylene glycol, polypropylene glycol, a copolymer of ethylene glycol and propylene glycol, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof.

In still another exemplary embodiment, F is an immunoglobulin Fc region.

In still another exemplary embodiment, F is an IgG Fc region.

In still another exemplary embodiment, L is selected from the group consisting of a peptide, a fatty acid, a saccharide, a polymer, a low molecular weight compound, a nucleotide, and a combination thereof.

In still another exemplary embodiment, the polymer is selected from the group consisting of polyethylene glycol, polypropylene glycol, a copolymer of ethylene glycol and propylene glycol, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof.

In still another exemplary embodiment, L is polyethylene glycol.

In still another exemplary embodiment, the polymer has molecular weight of 1 kDa to 100 kDa.

In still another exemplary embodiment, the linker is linked to the N-terminus of the B-chain of the insulin analog or a lysine residue in the insulin analog.

In still another exemplary embodiment, F is an immunoglobulin Fc region and the linker is linked to the N-terminus of the immunoglobulin Fc region.

In still another exemplary embodiment, F is an immunoglobulin Fc region and the conjugate has a structure in which both ends of the linker are linked to the N-terminus of the B-chain of the insulin analog and the N-terminus of the immunoglobulin Fc region.

In still another exemplary embodiment, the insulin analog is one in which a binding affinity to a native insulin receptor is reduced compared to native insulin.

In still another exemplary embodiment, the binding affinity of the insulin analog to the native insulin receptor is about 10% to about 90% compared to that of native insulin.

In still another exemplary embodiment, the conjugate is characterized in that F is an immunoglobulin Fc region; L is polyethylene glycol; and the binding affinity of the conjugate to the native insulin receptor is 0.1% to 50% compared to that of native insulin.

In still another exemplary embodiment, the conjugate is characterized in that F is an immunoglobulin Fc region; L is polyethylene glycol; and X is an insulin analog having a sequence identical to that of the native insulin except that the $14^{th}$ amino acid of the A-chain is aspartic acid.

Another aspect of the present invention provides a polynucleotide encoding the conjugate; a vector including the polynucleotide; and a transformant including the polynucleotide or the vector including the polynucleotide.

Still another aspect of the present invention provides a method for preparing the conjugate.

Still another aspect of the present invention provides a composition including the conjugate.

In an exemplary embodiment, the composition is a pharmaceutical composition.

In another exemplary embodiment, the composition is a pharmaceutical composition for preventing or treating an insulin-related disease.

In still another exemplary embodiment, the composition is a pharmaceutical composition for preventing or treating diabetes.

Still another aspect of the present invention provides a long-acting formulation with increased in vivo duration and/or stability compared to a conjugate of native insulin, including the conjugate of the insulin analog.

Still another aspect of the present invention provides a method for treating an insulin-related disease, which includes a step of administering the conjugate of the insulin analog or the composition thereof to a subject in need thereof.

In an exemplary embodiment, the insulin-related disease is diabetes.

Still another aspect of the present invention provides a use of the conjugate of the insulin analog in the preparation of a medicament.

In an exemplary, embodiment, the medicament is for the prevention or treatment of an insulin-related, disease.

In another exemplary embodiment, the medicament is for the prevention or treatment of diabetes.

Still another aspect of the present invention provides a use of the conjugate of the insulin analog in the treatment of an insulin-related disease, specifically diabetes.

Advantageous Effects

The non-native insulin analog conjugate of the present invention can improve compliance of patients in need of insulin administration.

DESCRIPTIONS OF THE DRAWINGS

FIG. 1 shows the analysis results of purity of insulin analogs by protein electrophoresis, and specifically, the results of representative insulin Analogs 9, 10, 11, and 12 (lane 1: fragment size marker; lane 2: native insulin; lane 3: insulin Analog 9; lane 4: insulin Analog 10; lane 5: insulin Analog 11; and lane 6: insulin Analog 12).

FIGS. 2a to 2d show the analysis results of the purity of insulin analogs by high-pressure chromatography, and specifically, the results in order of representative insulin analogs 9, 10, 11, and 12 (FIGS. 2a to 2d). In each drawing, the results of RP-HPLC (C18), RP-HPLC (C4), and SE-HPLC are shown in order from top to bottom.

FIGS. 3a to 3c are graphs showing the comparison results of the pharmacokinetic features between "insulin analog 10-PEG-immunoglobulin Fc conjugate", which is the representative insulin analog conjugate of the present invention, and "native insulin-PEG-immunoglobulin Fc conjugate", which is a native insulin conjugate, in normal mice (FIG. 3a), SD rats (FIG. 3b), and beagle dog (FIG. 3c).

FIG. 4 is a graph showing the comparison results of the blood glucose level-lowering ability between "insulin analog 10-PEG-immunoglobulin Fc conjugate", which is the representative insulin analog conjugate of the present invention, and "native insulin-PEG-immunoglobulin Fc conjugate", which is a native insulin conjugate, in DIO/STZ rats.

BEST MODE

Hereinbelow, exemplary embodiments of the present invention will be described in detail.

Meanwhile, each of the explanations and exemplary embodiments disclosed herein can be applied to other explanations and exemplary embodiments. That is, all combinations of various factors disclosed herein belong to the scope of the present invention. Furthermore, the scope of the present invention should not be limited by the specific disclosure provided hereinbelow.

Additionally, those skilled in the art will be able to recognize or confirm, based on routine experimentation, many equivalents to the specific embodiments of the present invention described in this application, and such equivalents are intended to be included in the present invention.

Throughout the entire specification, the conventional 1-letter and 3-letter codes for the amino acids are used. Additionally, the amino acids mentioned in abbreviations herein are described according to the IUPAC-IUB rules.

An aspect of the present invention provides an insulin analog conjugate.

Specifically, the insulin analog conjugate may be in the form of a conjugate in which an insulin analog is linked to a biocompatible material for increasing the in vivo half-life of the insulin analog. In the present invention, the biocompatible material may be interchangeably used with a carrier.

In the present invention, the insulin analog conjugate may exhibit an increased duration of the efficacy compared to the insulin analog to which a carrier is not conjugated, and such conjugate is designated as "long-acting conjugate" in the present invention.

Meanwhile, such conjugate may be a non-naturally occurring conjugate.

More specifically, the present invention provides a conjugate represented by the following Formula 1:

$$X\text{-}L_a\text{-}F \quad \text{[Formula 1]}$$

wherein in Formula 1,

X is an insulin analog comprising a modification of one or more amino acids selected from the group consisting of the $16^{th}$ amino acid of the B-chain, the $25^{th}$ amino acid of the B-chain, the $14^{th}$ amino acid of the A-chain, and the $19^{th}$ amino acid of the A-chain of native insulin;

L is a linker;

a is 0 or a natural number, with the proviso that when a is 2 or greater, each L is independent from each other; and F is a substance capable of increasing the half-life of X.

As used herein, the term "insulin analog" refers to non-native insulin which is different from native insulin. The insulin analog includes non-native human insulin which is different from native human insulin. The insulin analog is a moiety constituting the conjugate of the present invention, and corresponds to X in Formula 1.

Such an insulin analog includes analogs in which the some amino acids of native insulin is modified by addition, deletion, or substitution.

Specifically, compared to a sequence identity of the native insulin sequence, the insulin analog of the present invention may have a sequence identity of at least 60%, at least 65%, at least 70%, at least 75%, at least 80%, at least 85%, at least 90%, at least 91%, at least 92%, at least 93%, at least 94%, or at least 95%. Additionally, the insulin analog of the present invention may have a lower binding affinity to the native insulin receptor compared to that of the native insulin, while having the sequence identity above to the native insulin sequence. In addition, the insulin analog may have a glucose-absorbing ability and/or an ability to decrease blood glucose levels in vivo, as shown in the native insulin.

In the present invention, the binding affinity of any insulin analogs to the native insulin receptor refers to percentages of binding inhibitions exhibited in an insulin analog and native insulin when the binding inhibition levels are measured under a condition of competitive inhibition of receptor binding, in which the binding of any detector ligand to the native insulin receptor is inhibited in the presence of native insulin or an insulin analog corresponding thereto. The binding inhibition can indirectly be defined as values measured to determine whether the signals, which are shown due to the ligand binding of the insulin receptor according to appropriate criteria, changes effectively. For example, the binding affinity can be defined by the percentage of the measured value (e.g., the percentage of $IC_{50}$ of native insulin against IC$_{50}$ of an insulin analog corresponding thereto) obtained by measuring how much signals are increased or decreased; that is, when radioactive isotope-tagged insulin binds to the insulin receptor, the signals generated from this tag are measured to determine how much of each of the signals are reduced or increased after the addition of the untagged native insulin or insulin analog (e.g., by measuring the IC$_{50}$ values for signal reduction of native insulin or an insulin analog). Such measurement of the binding affinity of receptors through competitive inhibition is well known in the art. In an exemplary embodiment of the present invention, for the native insulin receptor required for such measurement, a cell membrane expressing a human native insulin receptor (A isoform or B isoform, or both), for example, a cell membrane of cells, which has been manipulated via a genetic engineering method to overexpress a human native insulin receptor may be used. In addition, for the detector ligand, native insulin tagged with iodine-125 may be used. In a more specific embodiment of the present invention, a scintillation proximity assay (SPA) may be used to measure the competitive inhibition of receptor binding. In a further specific embodiment of the present invention, the binding affinity to the insulin receptor may be measured using the method described in Experimental Example 1.

More specifically, compared with the binding affinity (100%) of native insulin to an insulin receptor, the insulin analog of the present invention may exhibit the binding affinity to the insulin receptor of about 99% or below, about 95% or below, about 90% or below, about 85% or below, about 80% or below, about 75% or below, about 70% or below, about 65% or below, about 60% or below, about 55% or below, about 50% or below, about 45% or below, about 40% or below, about 35% or below, about 30% or below, about 25% or below, about 20% or below, about 15% or below, about 10% or below, about 9% or below, about 8% or below, about 7% or below, about 6% or below, about 5% or below, about 4% or below, about 3% or below, about 2% or below, about 1% or below, or about 0.1% or below (however, the binding affinity of the insulin analog of the present invention to the insulin receptor does not correspond to 0%). In a specific embodiment of the present invention, the binding affinity of the insulin analog to the native insulin receptor is appropriately about 10% to about 90%, but the value is not limited thereto. In addition, if the binding affinity is weak relative to that of native insulin, the insulin analogue falls within the scope of the present invention. If the binding affinity is weaker than that of native insulin, removal of the insulin analog by the insulin receptor is weakened, and thus the improved blood half-life as well as sustainability of the effect can be expected.

In an embodiment of the present invention, in the insulin analog conjugate, the linker may be polyethylene glycol; the substance capable of increasing the half-life may be an immunoglobulin Fc region; and compared to the binding affinity of native insulin, the binding affinity to the native insulin receptor may be about 99% or below, about 95% or below, about 90% or below, about 85% or below, about 80% or below, about 75% or below, about 70% or below, about 65% or below, about 60% or below, about 55% or below, about 50% or below, about 45% or below, about 40% or below, about 35% or below, about 30% or below, about 25% or below, about 20% or below, about 15% or below, about 10% or below, about 9% or below, about 8% or below, about 7% or below, about 6% or below, about 5% or below, about 4% or below, about 3% or below, about 2% or below, about 1% or below, or about 0.1% or below (however, the binding affinity of the insulin analog conjugate of the present invention to the insulin receptor does not correspond to 0%). In a specific embodiment of the present invention, the binding affinity of the insulin analog conjugate to the native insulin receptor is suitably 0.1% to 50%, but the value is not limited thereto. In addition, if the binding affinity is weaker than that of native insulin, it falls within the scope of the present invention. If the binding affinity is weaker than that of native insulin, removal of the insulin analog conjugate by the insulin receptor is weakened, and thus the improved blood half-life as well as sustainability of the effect can be expected.

As used herein, the term "about" refers to a range including ±0.5, ±0.4, ±0.3, ±0.2, ±0.1, etc., and thus includes all of the values in the range equivalent or similar to those stated after this term, but is not limited thereto.

Additionally, the insulin analog of the present invention may possess the glucose-uptake ability as shown in native insulin.

Specifically, the insulin analog according to the present invention may have a glucose-uptake ability of about 10% or higher, about 20% or higher, about 30% or higher, about 40% or higher, about 50% or higher, about 55% or higher, about 60% or higher, about 65% or higher, about 70% or higher, about 75% or higher, about 80% or higher, about 85% or higher, about 90% or higher, about 95% or higher, about 100% or higher, about 110% or higher, about 120% or higher, about 130% or higher, about 140% or higher, about 150% or higher, about 160% or higher, about 170% or higher, about 180% or higher, about 190% or higher, or about 200% or higher, relative to the glucose-uptake ability (100%) of native insulin.

The measurement of the glucose-uptake ability can be achieved using various methods for measuring glucose-uptake abilities known in the art.

Specifically, the insulin analog may be a single chain in which each of two sequence regions corresponding to the A-chain and B-chain of its native form is linked in one polypeptide chain, or may be in the form of two polypeptide chains where two sequence regions are each composed of individual polypeptide chains. Hereinafter, when the A-chain or B-chain of the insulin analog is referred to in the present specification, it should be construed depending on the situation that it refers to the A-chain or B-chain when the corresponding insulin analog is in the form of two polypeptide chains, and that it refers to a sequence region corresponding to the native A-chain in the corresponding single-chain polypeptide or a sequence region corresponding to the native B-chain in the corresponding single chain polypeptide, respectively, even when the analog is in the form of a single chain. The insulin analog of the present invention may be in the form of a single chain or two polypeptide chains, which is a combination of one chain selected from the A-chain of native insulin or a polypeptide corresponding thereto and one chain selected from the B-chain of native insulin or a polypeptide corresponding thereto. In particular, corresponding to the A-chain or B-chain of native insulin may refer to cases, for example, in which any one chain of the polypeptides of the two polypeptide chains has a sequence identify of at least 60%, at least 65%, at least 70%, at least 75%, at least 80%, at least 85%, at least 90%, at least 91%, at least 92%, at least 93%, at least 94%, or at least 95%, compared to that of the A-chain or B-chain of native insulin, but is not particularly limited thereto, and those skilled in the art can easily determine the same by comparison between the sequence constituting the corresponding polypeptide and that of the A-chain or B-chain of native insulin.

As described above, the contents described herein are intended to apply to all of the descriptions relevant to the sub-concepts of the insulin analog.

Native insulin is a hormone secreted by the pancreas and generally has the role of promoting intracellular glucose uptake and inhibiting fat breakdown, thereby controlling in vivo blood glucose levels. Insulin, which can control blood glucose levels, is generated from the processing of its precursor, proinsulin, which does not have the function of controlling blood glucose levels. Insulin is composed of two polypeptide chains, i.e., the A-chain and the B-chain, which include 21 and 30 amino acids, respectively, and are interlinked by two disulfide bridges. Each of the A-chain and the B-chain may include the amino acid sequences represented by SEQ ID NOS: 53 and 54 shown below.

```
A-chain:
                                       (SEQ ID NO: 53)
Gly-Ile-Val-Glu-Gln-Cys-Cys-Thr-Ser-Ile-Cys-Ser-
Leu-Tyr-Gln-Leu-Glu-Asn-Tyr-Cys-Asn B-chain:
                                       (SEQ ID NO: 54)
Phe-Val-Asn-Gln-His-Leu-Cys-Gly-Ser-His-Leu-Val-
Glu-Ala-Leu-Tyr-Leu-Val-Cys-Gly-Glu-Arg-Gly-Phe-
Phe-Tyr-Thr-Pro-Lys-Thr
```

In an exemplary embodiment, the insulin analogs described in the present invention may be those with a reduced binding affinity to receptors while having the function of controlling the in vivo blood glucose levels like the native insulin. More specifically, the insulin analog may possess the ability of lowering in vivo blood glucose levels.

Additionally, in an exemplary embodiment, the kind and size of the insulin analogs may not be particularly limited as long as they can exhibit the reduced receptor-mediated internalization or receptor-mediated clearance. Accordingly, the insulin analogs of the present invention can exhibit improved half-life in the blood compared to native insulin.

The insulin analogs of the present invention include inverted insulin, derivatives of native insulin, fragments of native insulin, etc. The insulin analogs can be prepared not only by a genetic recombination method but also by a solid phase synthesis, and the preparation method is not limited thereto.

As used herein, the term "derivatives of native insulin" refers to a peptide which has at least one difference in the amino acid sequence compared to that of the native insulin, a peptide prepared by modification of the native insulin sequence, and a native insulin mimic which can control the in vivo blood glucose levels like the native insulin. Such derivatives of native insulin may be those which have the function of controlling in vivo blood glucose levels.

Specifically, the derivatives of native insulin may be prepared via modification by any one method of substitution, addition, deletion, modification or a combination of the methods in a part of the amino acid of the native insulin.

Specifically, the derivatives of native insulin may have a homology of 80% or higher to each of the amino acid sequences of the A-chain and the B-chain of native insulin and/or a part of the groups in an amino acid residue may be modified by chemical substitution (e.g., alpha-methylation, alpha-hydroxylation), deletion (e.g., deamination), or modification (e.g., N-methylation), etc., but are not limited thereto.

The derivatives of native insulin applied in the present invention may be prepared by a combination of various methods used for preparing derivatives.

Additionally, such modification for the preparation of the derivatives of native insulin includes a modification using L-type or D-type amino acid(s), and/or non-natural amino acid(s); and/or a modification of the native sequence or post-translational modification (e.g., methylation, acylation, ubiquitination, intermolecular covalent bond, etc.).

Additionally, the derivatives of native insulin all include those in which one or more amino acids are added to the amino and/or carboxy end of the native insulin.

For the substitution or insertion of the amino acid(s), not only the 20 amino acids conventionally observed in human proteins but also atypical or unnatural amino acids may be used. The commercial origin of the atypical amino acids may include Sigma-Aldrich, ChemPep, Genzyme pharmaceuticals, etc. The sequences of the peptides containing these amino acids and typical peptides may be synthesized by or purchased from commercial peptide synthesis companies, such as American Peptide Company, Bachem (USA), and Anygen (Korea), but are not particularly limited thereto.

As used herein, the term "fragments of native insulin or fragments of derivatives of native insulin" refers to a form of insulin in which at least one amino acid at the amino end or carboxy end of native insulin or a derivative of native insulin is removed. Such insulin fragment can possess the function of controlling in vivo blood glucose levels.

Additionally, the insulin analogs of the present invention may be those which were prepared using the method(s) for preparing the derivatives and fragments of the native insulin independently or in combination.

Specifically, the insulin analogs according to the present invention may include those having a modification in the A-chain and B-chain of native insulin described above, and specifically, those in which a particular amino acid residue(s) of the A-chain of native insulin is(are) modified and/or a particular amino acid residue(s) of the B-chain of native insulin is(are) modified.

Specifically, the insulin analogs may be those in which at least one modification in an amino acid, which is selected from the group consisting of the $16^{th}$ amino acid of the B-chain of native insulin, the $25^{th}$ amino acid of the B-chain, the $14^{th}$ amino acid of the A-chain, and the $19^{th}$ amino acid of the A-chain of native insulin, is substituted with a different amino acid, and specifically, it may be substituted with glutamic acid, serine, threonine, aspartic acid, histidine, lysine, or alanine, but is not limited thereto.

Specifically, the insulin analogs may be those in which at least one, at least two, at least three, or four amino acids among the amino acids described above is (are) substituted with other amino acid(s).

Specifically, the modification may be a modification of the $16^{th}$ amino acid of the B-chain of insulin (i.e., tyrosine) into glutamic acid, serine, threonine, or aspartic acid; a modification of the $25^{th}$ amino acid of the B-chain of insulin (i.e., phenylalanine) into aspartic acid or glutamic acid; a modification of the $14^{th}$ amino acid of the A-chain of insulin (i.e., tyrosine) into histidine, lysine, alanine, or aspartic acid; or a modification of the $19^{th}$ amino acid of the A-chain of insulin (i.e., tyrosine) into glutamic acid, serine, or threonine.

Therefore, the insulin analog may include a modification of the $16^{th}$ amino acid of the B-chain of native insulin (i.e., tyrosine) into glutamic acid, serine, threonine, or aspartic acid; and/or a modification of the $25^{th}$ amino acid of the B-chain of native insulin (i.e., phenylalanine) into aspartic acid or glutamic acid; and/or a modification of the $14^{th}$ amino acid of the A-chain of native insulin (i.e., tyrosine) into histidine, lysine, alanine, or aspartic acid; and/or a modification of the 19th amino acid of the A-chain of native insulin (i.e., tyrosine) into glutamic acid, serine, or threonine, but these are not limited thereto.

More specifically, the insulin analogs may be those including the A-chain of SEQ ID NO: 55 represented by General Formula 2 below and the B-chain of SEQ ID NO: 56 represented by General Formula 3 below. These insulin analogs may be in the form where the A-chain and the B-chain are interlinked by a disulfide bond, or in the form of a proinsulin, but are not limited thereto.

[General Formula 2]
(SEQ ID NO: 55)
Xaa1-Ile-Val-Glu-Xaa5-Cys-Cys-Thr-Ser-Ile-Cys-Xaa12-Leu-Xaa14-Gln-Xaa16-Glu-Asn-Xaa19-Cys-Xaa21 in General Formula 2,

Xaa1 is alanine, glycine, glutamine, histidine, glutamic acid, or asparagine;

Xaa5 is alanine, glutamic acid, glutamine, histidine, or asparagine;

Xaa12 is alanine, serine, glutamine, glutamic acid, histidine, or asparagine;

Xaa14 is tyrosine, histidine, lysine, alanine, or aspartic acid;

Xaa16 is alanine, leucine, tyrosine, histidine, glutamic acid, or asparagine;

Xaa19 is tyrosine, glutamic acid, serine, or threonine; and

Xaa21 is asparagine, glycine, histidine, or alanine.

[General Formula 3]
(SEQ ID NO: 56)
Phe-Val-Asn-Gln-His-Leu-Cys-Gly-Ser-His-Leu-Val-Gln-Ala-Leu-Xaa16-Leu-Val-Cys-Gly-Glu-Arg-Gly-Phe-Xaa25-Tyr-Xaa27-Xaa28-Lys-Thr in General Formula 3, Xaa16 is tyrosine, glutamic acid, serine, threonine, or aspartic acid;

Xaa25 is phenylalanine, aspartic acid, or glutamic acid;

Xaa27 is threonine or is absent; and

Xaa28 is proline, glutamic acid, or aspartic acid, or is absent.

Herein, the peptides where the A-chain coincides with SEQ ID NO: 53 while the B-chain also coincides with SEQ ID NO: 54 may be excluded.

Additionally, those peptides which have a homology of 70% or higher, specifically 80% or higher, more specifically 90% or higher, and even more specifically 95% or higher to the sequence of the corresponding insulin analog including the A-chain of General Formula 2 above and the B-chain of General Formula 3 above, while including the characteristic modification (i.e., amino acid residues not present in native insulin) of the 14th and/or the 19th amino acids of the A-chain, and/or the 16th and/or the 25th amino acids of the B-chain described above, and have a reduced binding affinity to receptors compared to the native insulin are also included in the scope of the present invention.

As used herein, the term "homology" refers to a level of similarity with regard to the amino acid sequence of a wild type protein or a polynucleotide sequence encoding the same, and includes the sequences having a sequence with the above percentage or higher of the same sequence with the amino acid sequence or polynucleotide sequence of the present invention. This homology may be determined via comparison by the naked eye, or may be determined via a bioinformatic algorithm which analyzes the degree of homology by arranging the two sequences. The homology between the two amino acid sequences may be indicated as a percentage. Useful automated algorithms can be used in both GAP, BESTFIT, and FASTA of Wisconsin Genetics Software Package (Genetics Computer Group, Madison, Wis., USA) and TFASTA computer software modules. The automated array algorithms include the sequence array algorithms of Needleman & Wunsch, Pearson & Lipman, and Smith & Waterman. The determination of algorithm and homology is automated in software including FASTP, BLAST, BLAST2, PSIBLAST, and CLUSTAL W.

In an exemplary embodiment, the insulin analog may be an insulin analog including the A-chain of SEQ ID NO: 55 represented by General Formula 2 above and the B-chain of SEQ ID NO: 54; or an insulin analog including the A-chain of SEQ ID NO: 53 and the B-chain of SEQ ID NO: 56 represented by General Formula 3 above, but is not particularly limited thereto.

More specifically, the insulin analog may be an insulin analog, wherein in General Formula 2, Xaa1 is glycine, Xaa5 is glutamine, Xaa12 is serine, Xaa14 is tyrosine, histidine, lysine, alanine, or aspartic acid, Xaa16 is leucine, Xaa19 is tyrosine, glutamic acid, serine, or threonine, and Xaa21 is asparagine; and in General Formula 3, Xaa16 is tyrosine, glutamic acid, serine, threonine, or aspartic acid, Xaa25 is phenylalanine, aspartic acid, or glutamic acid, Xaa27 is threonine, and Xaa28 is proline, but is not limited thereto.

More specifically, the insulin analog may be an insulin analog, wherein in General Formula 2, Xaa1 is glycine, Xaa5 is glutamine, Xaa12 is serine, Xaa14 is tyrosine, Xaa16 is leucine, Xaa19 is tyrosine, glutamic acid, or serine, and Xaa21 is asparagine; and in General Formula 3, Xaa16 is tyrosine, glutamic acid, serine, or aspartic acid, Xaa25 is phenylalanine, aspartic acid, or glutamic acid, Xaa27 is threonine, and Xaa28 is proline, but is not limited thereto.

More specifically, the insulin analog may be an insulin analog, wherein in General Formula 2, Xaa1 is glycine, Xaa5 is glutamine, Xaa12 is serine, Xaa14 is tyrosine or aspartic acid, Xaa16 is leucine, Xaa19 is tyrosine, glutamic acid, serine, or threonine, and Xaa21 is asparagine; and in General Formula 3, Xaa16 is tyrosine, Xaa25 is phenylalanine, aspartic acid, or glutamic acid, Xaa27 is threonine, and Xaa28 is proline, but is not limited thereto.

In an exemplary embodiment, the insulin analog according to the present invention may correspond to the following insulin analogs:

(1) in General Formula 2, Xaa1 is glycine, Xaa5 is glutamine, Xaa12 is serine, Xaa14 is histidine, Xaa16 is leucine, Xaa19 is tyrosine, and Xaa21 is asparagine; and in General Formula 3, Xaa16 is tyrosine, Xaa25 is phenylalanine, Xaa27 is threonine, and Xaa28 is proline;

(2) in General Formula 2, Xaa1 is glycine, Xaa5 is glutamine, Xaa12 is serine, Xaa14 is lysine, Xaa16 is leucine, Xaa19 is tyrosine, and Xaa21 is asparagine; and in General Formula 3, Xaa16 is tyrosine, Xaa25 is phenylalanine, Xaa27 is threonine, and Xaa28 is proline;

(3) in General Formula 2, Xaa1 is glycine, Xaa5 is glutamine, Xaa12 is serine, Xaa14 is tyrosine, Xaa16 is leucine, Xaa19 is glutamic acid, and Xaa21 is asparagine; and in General Formula 3, Xaa16 is tyrosine, Xaa25 is phenylalanine, Xaa27 is threonine, and Xaa28 is proline;

(4) in General Formula 2, Xaa1 is glycine, Xaa5 is glutamine, Xaa12 is serine, Xaa14 is tyrosine, Xaa16 is leucine, Xaa19 is serine, and Xaa21 is asparagine; and in General Formula 3, Xaa16 is tyrosine, Xaa25 is phenylalanine, Xaa27 is threonine, and Xaa28 is proline;

(5) in General Formula 2, Xaa1 is glycine, Xaa5 is glutamine, Xaa12 is serine, Xaa14 is tyrosine, Xaa16 is leucine, Xaa19 is threonine, and Xaa21 is asparagine; and in General Formula 3, Xaa16 is tyrosine, Xaa25 is phenylalanine, Xaa27 is threonine, and Xaa28 is proline;

(6) in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is glutamic acid, Xaa25 is phenylalanine, Xaa27 is threonine, and Xaa28 is proline;

(7) in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is serine, Xaa25 is phenylalanine, Xaa27 is threonine, and Xaa28 is proline;

(8) in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is threonine, Xaa25 is phenylalanine, Xaa27 is threonine, and Xaa28 is proline;

(9) in General Formula 2, Xaa1 is glycine, Xaa5 is glutamine, Xaa12 is serine, Xaa14 is alanine, Xaa16 is leucine, Xaa19 is tyrosine, and Xaa21 is asparagine; and in General Formula 3, Xaa16 is tyrosine, Xaa25 is phenylalanine, Xaa27 is threonine, and Xaa28 is proline;

(10) in General Formula 2, Xaa1 is glycine, Xaa5 is glutamine, Xaa12 is serine, Xaa14 is aspartic acid, Xaa16 is leucine, Xaa19 is tyrosine, and Xaa21 is asparagine; and in General Formula 3, Xaa16 is tyrosine, Xaa25 is phenylalanine, Xaa27 is threonine, and Xaa28 is proline;

(11) in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is aspartic acid, Xaa25 is phenylalanine, Xaa27 is threonine, and Xaa28 is proline;

(12) in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is tyrosine, Xaa25 is aspartic acid, Xaa27 is threonine, and Xaa28 is proline; and (13) in General Formula 2, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 3, Xaa16 is tyrosine, Xaa25 is glutamic acid, Xaa27 is threonine, and Xaa28 is proline.

Additionally, in an exemplary embodiment, the insulin analog may be an insulin analog including an amino acid sequence selected from the group consisting of SEQ ID NOS: 28, 30, 32, 34, 36, 38, 40, 42, 44, 46, 48, 50, and 52, but is not limited thereto.

The insulin analog according to the present invention may be one including the specific sequence described above, and one consisting (essentially) of the above-described specific sequence, but is not limited to.

Additionally, although it is described as "peptide consisting of a specific SEQ ID NO" in the present invention, it does not exclude any addition of nonsense sequences upstream or downstream of the amino acid sequence of the corresponding SEQ ID NO or naturally-occurring mutations, or silent mutations thereof, as long as the peptide has the same or equivalent activity as the peptide consisting of the amino acid sequence of the corresponding SEQ ID NO, and it is obvious that a peptide including such a sequence addition or mutation is also within the scope of the present invention.

Meanwhile, the insulin analog includes all of the peptide itself, salts thereof (e.g., a pharmaceutically acceptable salt of the peptide), or solvates thereof.

Additionally, the peptide may be in any pharmaceutically acceptable form.

The kind of the salt is not particularly limited. However, it is preferable that the salt be in a safe and effective form for a subject (for example, mammals), but is not particularly limited thereto.

As used herein, the term "pharmaceutically acceptable" refers to a material which can be effectively used for a desired purpose without causing excessive toxicity, irritation, allergic response, etc., within the scope of pharmaco-medical decision.

As used herein, the term "pharmaceutically acceptable salt" includes a salt derived from pharmaceutically acceptable inorganic acids, organic acids, or bases. Examples of the suitable acids may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Salts derived from suitable bases may include alkali metals such as sodium, potassium, etc., alkaline earth metals such as magnesium, etc., ammonium, etc.

Additionally, as used herein, the term "solvate" refers to a complex which is formed between the peptide according to the present invention or a salt thereof and a solvent molecule.

The insulin analogs may be easily produced by those skilled in the art using peptide preparation methods known in the art. For example, the insulin analogs can be produced by a method including the following steps:

a) expressing an insulin analog by culturing a transformant including the nucleic acid encoding the insulin analog; and b) isolating and purifying the expressed insulin analog.

The medium used in culturing the transformants in the present invention may meet the requirements for host cell cultivation in an appropriate manner. The carbon sources to be contained in the medium for the growth of a host cell may be appropriately selected by a skilled person in the art according to the transformants prepared thereof, and appropriate cultivation conditions may be selected to control the period and amount of cultivation.

Examples of the sugar source to be used may include sugars and carbohydrates such as glucose, saccharose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These materials may be used alone or in combination.

Examples of the nitrogen source to be used may include peptone, yeast extract, meat gravy, malt extract, corn steep liquor, soybean flour, and urea, or inorganic compounds such as ammonium sulfate, ammonium chloride, ammonium phosphate, ammonium carbonate, and ammonium nitrate. The nitrogen source may also be used alone or in combination.

Examples of the phosphorous source to be used may include potassium dihydrogen phosphate or dipotassium hydrogen phosphate or a corresponding sodium-containing salt. Additionally, the culture media may contain a metal salt such as magnesium sulfate or iron sulfate necessary for the growth of the transformant.

Lastly, essential growth materials such as amino acids and vitamins may be used. Additionally, appropriate precursors for culture media may also be used. The above sources may be appropriately added to a culture during cultivation by a batch culture or continuous culture. The pH of the culture may be appropriately adjusted using a basic compound such as sodium hydroxide, potassium hydroxide, and ammonia, or an acid compound such as phosphoric acid or sulfuric acid. Additionally, an antifoaming agent such as fatty acid polyglycol ester may be added to prevent foam generation. Additionally, in order to maintain the aerobic state of the culture, oxygen or an oxygen-containing gas (e.g., air) may be injected into the culture.

The transformant of the present invention may be cultured at 20° C. to 45° C., and specifically, 25° C. to 40° C. Additionally, the cultivation is continued until the maximum amount of production of the desired insulin analogs is obtained, and in this regard, the cultivation may normally be continued for 10 hours to 160 hours.

As described above, the transformant of the present invention can produce insulin analogs when appropriate culture conditions are provided according to host cells, and the insulin analogs produced may be secreted within the cytoplasm or into the periplasmic space of the host cell or extracellularly according to the vector constitution and characteristics of a host cell.

The proteins expressed within or outside of the host cell may be purified by a conventional method. Examples of the purification method may include salting-out (e.g., ammonium sulfate precipitation, sodium phosphate precipitation, etc.), solvent precipitation (e.g., protein fraction precipitation using acetone or ethanol, etc.), dialysis, gel filtration, chromatography such as ion-exchange chromatography, or reversed column chromatography, ultrafiltration, etc. and these methods may be used alone or in combination.

In an exemplary embodiment, the present invention may further include the following steps for separation and purification of the insulin analog expressed in the form of inclusion bodies from the transformant:

b-1) obtaining the transformant from the culture in step a) and pulverizing the same;

b-2) recovering the expressed insulin analog from the pulverized cell lysate followed by refolding the same;

b-3) purifying the refolded insulin analog by cation exchange chromatography;

b-4) treating the purified insulin analog with trypsin and carboxypeptidase B; and b-5) sequentially purifying the treated insulin analog by cation exchange chromatography, and anion exchange chromatography or reversed-phase chromatography.

In the present invention, the nucleic acid encoding the insulin analog includes the nucleotide sequences represented by SEQ ID NOS: 27, 29, 31, 33, 35, 37, 39, 41, 43, 45, 47, 49, or 51. In an exemplary embodiment, the nucleic acid of the present invention not only includes the nucleotide sequences represented by SEQ ID NOS: 27, 29, 31, 33, 35, 37, 39, 41, 43, 45, 47, 49, or 51, but also includes all sequences which have a sequence homology of at least 70% to the above sequences, preferably at least 80%, more preferably at least 90%, even more preferably at least 95%, and most preferably at least 98%, in which the peptide encoded by the above nucleic acid exhibits a reduced binding affinity to receptors compared to the native insulin while substantially having the function of controlling in vivo blood glucose levels.

The recombinant vector according to the present invention may be constructed as a typical vector for cloning or for expression, and may be constructed as a vector using a eukaryotic cell or prokaryotic cell as a host cell.

As used herein, the term "vector" refers to a recombinant vector capable of expressing a target protein in an appropriate host cell, which is a nucleic acid construct including essential regulatory factors operably linked to enable the expression of a nucleic acid insert. The present invention can prepare a recombinant vector which includes a nucleic acid encoding an insulin analog, and the insulin analog of the present invention may be obtained via transformation or transfection of the recombinant vector into a host cell.

In the present invention, the nucleic acid encoding the insulin analog can be operably linked to a promoter.

The method for transforming the recombinant vector including a nucleic acid encoding an insulin analog according to the present invention may not be limited to these methods, but any method for transformation or transfection commonly used in the art may be used without limitation.

The transformant of the present invention may be obtained by introducing a recombinant vector including the target nucleic acid which encodes an insulin analog into a host cell.

An appropriate host to be used in the present invention may not be particularly limited as long as it can express the nucleic acid of the present invention. Examples of the appropriate host may include a bacteria belonging to the genus *Escherichia* such as *E. coli*, a bacteria belonging to the genus *Bacillus* such as *Bacillus subtilis*, a bacteria belonging to the genus *Pseudomonas* such as *Pseudomonas putida*, yeasts such as *Pichia pastoris, Saccharomyces cerevisiae*, and *Schizosaccharomyces pombe*, an insect cell such as *Spodoptera frugiperda* (SF9), and animal cells such as CHO, COS, and BSC. Specifically, *E. coli* may be used as a host cell, but the host is not limited thereto.

Meanwhile, F in the conjugate is a substance capable of increasing the half-life of X, and corresponds to a constituent of a moiety constituting the conjugate of the present invention.

F and X may be linked to each other by a covalent chemical bond or non-covalent chemical bond, and alternately, F and X may be linked to each other by a covalent chemical bond, non-covalent chemical bond, or combination thereof.

More specifically, X and L, and L and F may be linked to each other via a covalent bond. Herein, the conjugate is a conjugate in which X, L, and F are linked to each other via a covalent bond in the order of Formula 1.

The substance capable of increasing the half-life of X may be a biocompatible material, and for example, it may be selected from the group consisting of a polymer, a fatty acid, cholesterol, albumin and a fragment thereof, an albumin-binding material, a polymer of repeating units of a particular amino acid sequence, an antibody, an antibody fragment, an FcRn-binding material, an in vivo connective tissue, a nucleotide, fibronectin, transferrin, saccharide, heparin, and elastin, but is not particularly limited thereto.

For the elastin, it may be a human tropoelastin which is a water-soluble precursor, and may be a polymer of a part of the sequence or a part of repeating units thereof. For example, the elastin may include an elastin-like polypeptide, but is not particularly limited thereto.

Examples of the polymer include a polymer selected from the group consisting of polyethylene glycol (PEG), polypropylene glycol, a copolymer of ethylene glycol and propylene glycol, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof, but is not particularly limited thereto.

Polyethylene glycol is a term collectively including all forms of ethylene glycol homopolymer, PEG copolymer, or monomethyl-substituted PEG (mPEG) polymer, but is not particularly limited thereto.

Additionally, the biocompatible material includes poly-amino acids such as poly-lysine, poly-aspartic acid, and poly-glutamic acid, but is not limited thereto.

Additionally, the fatty acid may be one having binding ability to albumin in the body, but is not particularly limited thereto.

As a more specific example, the FcRn-binding material may be an immunoglobulin Fc region, and more specifically, an IgG Fc region, but is not particularly limited thereto.

In order to increase the in vivo solubility and/or to enhance the half-life and/or the bioavailability of the insulin analog, the biocompatible material can be linked to side chain of one or more amino acids in the insulin analog of the present invention. Such modifications may also reduce the clearance of therapeutic proteins and peptides.

The biocompatible material describe above may be water-soluble (amphipathic or hydrophilic) and/or non-toxic, and/or pharmaceutically acceptable.

F may be directly linked to X (i.e., a in Formula 1 is 0), or may be linked to X via a linker (L).

Specifically, L may be a peptide linker or a non-peptide linker.

When L is a peptide linker, it may include one or more amino acids, for example, 1 to 1000 amino acids, but is not particularly limited thereto. In the present invention, various known peptide linkers may be used in order to link F to X. For example, a [GS]$_x$ linker, a [GGGS]$_x$ linker (SEQ ID NO: 57), a [GGGGS]$_x$ linker (SEQ ID NO: 58), etc. may be included, and x in the linkers above may be a natural number greater than or equal to 1. However, the linkers are not limited to the examples above.

In the present invention, "the non-peptide linker" includes a biocompatible polymer having two or more repeating units linked to each other. The repeating unites are linked by any covalent bond excluding the peptide bond. The non-peptide linker may be a constituent of a moiety of the conjugate of the present invention, and corresponds to L in Formula 1. In the present invention, when L is a biocompatible polymer as a non-peptide linker, a linking element for linking the linker L with the insulin analog X and/or F via a covalent bond can be further included in the distal end of the non-peptide linker. Such linking element is not particularly limited as long as it is an atom or an atomic group, which is not a repeating unit of the biocompatible polymer, and is suitable for linking the biocompatible polymer with X and/or F via a covalent bond.

In L$_a$, a may be 1 or more, and each L may be independent when a is 2 or more.

In the present invention, the non-peptide linker can interchangeably be used with a non-peptide polymer.

In addition, in an exemplary embodiment, the conjugate may be one in which F and X are covalently linked to each other via a non-peptide linker including a reactive group capable of conjugating F, specifically an immunoglobulin Fc region, and X on both ends.

Specifically, the non-peptide linker may be selected from the group consisting of fatty acids, saccharides, polymers, low molecular weight compounds, nucleotides, and combinations thereof.

The polymer of the present invention may be in the range of more than 0 kDa to about 100 kDa, specifically in the range of about 1 kDa to about 100 kDa, and more specifically in the range of about 1 kDa to about 20 kDa, but is not particularly limited thereto.

The non-peptide linker may be selected from the group consisting of a biodegradable polymer such as polyethylene glycol, polypropylene glycol, a copolymer of ethylene glycol and propylene glycol, polyoxyethylated polyol, polyvinyl alcohol, a polysaccharide, dextran, polyvinyl ethyl ether, polylactic acid (PLA), and polylactic-glycolic acid (PLGA), and a lipid polymer, chitin, hyaluronic acid, oligonucleotide, and a combination thereof, but is not particularly limited thereto.

In an exemplary embodiment, the non-peptide polymer may be polyethylene glycol, but is not limited thereto. In addition, derivatives thereof which are already known in the art and those which can be easily prepared by techniques known in the art are also included in the scope of the present invention.

The non-peptide linker can be used in the present invention without limitation as long as it is a polymer having resistance to an in vivo proteolytic enzyme. The molecular weight of the non-peptide polymer is in the range of greater than 0 kDa to about 100 kDa, specifically in the range of about 1 kDa to about 100 kDa, and more specifically in the range of about 1 kDa to about 20 kDa, but is not limited thereto.

As used herein, the term "about" refers to a range including ±0.5, ±0.4, ±0.3, ±0.2, ±0.1, etc., and may include all of the values in the range equivalent to or similar to those stated after this term, but is not limited thereto.

Additionally, as the non-peptide linker of the present invention, which is to be linked to the polypeptide corresponding to F, not only one kind of polymer but also a combination of different kinds of polymers may be used.

As stated above, in an exemplary embodiment, both ends of the non-peptide linker may be each linked to F and X through the linking element. For example, in a specific embodiment of the present invention, the insulin analog conjugate of the present invention is prepared by reacting (linking reaction) an immunoglobulin Fc region and/or an insulin analog with a non-peptide polymer (a non-peptide polymer possessing a reactive group) having a reactive group capable of forming a covalent bond (i.e., the reactive group is converted to the linking element of the conjugate) with an amine group or thiol group of an immunoglobulin Fc region and an amine or thiol group of X through a chemical reaction at its terminus. That is, the non-peptide polymer possessing a reactive group becomes a non-peptide linker constituting a part of the conjugate by a linking reaction. Herein, the non-peptide linker in the conjugate consists of repeating units and a linking element of the non-peptide polymer possessing a reactive group.

Specifically, as the non-peptide polymer possessing a reactive group capable of being used for preparation of the conjugate, the non-peptide polymer may include a reactive group which can be linked to F (e.g., an immunoglobulin Fc region) and X at both ends thereof, respectively, and specifically a reactive group which can be linked to an amine group located at the N-terminus or a lysine residue or a thiol group in a cysteine residue of X; or an amine group located at the N-terminus of or a lysine residue or a thiol group in a cysteine residue of F (e.g., an immunoglobulin Fc region), but the reactive group is not limited thereto.

Additionally, the reactive group of the non-peptide polymer which can form a covalent bond with F, i.e., an immunoglobulin Fc region, and X may be selected from the group consisting of an aldehyde group, a maleimide group, and a succinimide derivative, but is not limited thereto.

In the above, a propionaldehyde group or a butyraldehyde group may be included as an example of the aldehyde group, but the aldehyde group is not limited thereto.

The succinimide derivative may include succinimidyl valerate, succinimidyl methylbutanoate, succinimidyl methylpropionate, succinimidyl butanoate, succinimidyl propionate, N-hydroxysuccinimide, hydroxysuccinimidyl, succinimidyl carboxymethyl, or succinimidyl carbonate, but is not limited thereto.

The non-peptide linker may be linked to X and F via such a linking element through the conversion of the reactive group, but is not particularly limited thereto.

Additionally, the final product produced by reductive amination with an aldehyde bond is much more stable than with an amide bond. The aldehyde reactive group selectively reacts at the N-terminus at low pH, and may form a covalent bond with the lysine residues at high pH, e.g., pH 9.0.

Additionally, the reactive groups at both ends of the non-peptide polymer having a reactive group may be the same or different from each other; for example, it may have a maleimide group at one end and an aldehyde group, a propionaldehyde group, or a butyraldehyde group at the other end. However, the reactive groups are not particularly limited as long as F (i.e., an immunoglobulin Fc region) and X can be linked at both ends of the non-peptide polymer having a reactive group.

For example, a maleimide group may be included as a reactive group at one end of the non-peptide polymer having a reactive group; and an aldehyde group, a propionaldehyde group, a butyraldehyde group, etc. may be included as a reactive group at the other end of the non-peptide polymer.

When polyethylene glycol having a hydroxy reactive group at both ends is used as the non-peptide polymer, the hydroxy group can be activated using chemical reactions known in the art to produce various reactive groups described above, or the long-acting protein conjugate of the present invention can be prepared using polyethylene glycol having a commercially available modified reactive group.

In an exemplary embodiment, the non-peptide polymer may be one linked to X, e.g., the N-terminal region or lysine residue of the insulin analog, but is not particularly limited thereto. Specifically, the non-peptide polymer, e.g., PEG, may be linked to the N-terminal region of the insulin analog, e.g., the amine group of the terminal amino acid or the amine group of lysine present in the insulin analog, but it is not particularly limited thereto.

Additionally, in an exemplary embodiment, the non-peptide polymer may be linked to the N-terminal region of F, e.g., the immunoglobulin Fc, but is not particularly limited thereto. Specifically, the non-peptide polymer may be linked to the N-terminal region of the immunoglobulin Fc, specifically to the amine group of the terminal amino acid, but it is not particularly limited thereto.

As used herein, the term "N-terminal region" refers to an amino terminal region of an insulin analog or an immunoglobulin Fc, and also refers to a position which can be linked to the linker for the purpose of the present invention. For example, the N-terminal region may include not only the terminal amino acid residues of the N-terminal region but also the amino acid residues near the N-terminal amino acid residues, and specifically may include the 1$^{st}$ to 20$^{th}$ amino acid residues from the distal end, but is not particularly limited thereto.

If an aldehyde group exists at one end of the non-peptide polymer having a reactive group, and links to an amine group located at the N-terminus of the insulin analog, the aldehyde group can be linked to the amine group through a reductive amination reaction. In addition, if an aldehyde is present at the other end of the non-peptide polymer having a reactive group, and links to an amine group located at the N-terminus of the immunoglobulin Fc, the aldehyde group can also be linked to the amine group through a reductive amination reaction.

In an embodiment of the present invention, the non-peptide polymer having a reactive group, which was used for the preparation of the conjugate, is PEG having a reactive group at both ends, and thus the conjugate is formed by linking the non-peptide polymer to an amino group of X and F via reductive amination. Herein, the conjugate has the following structure:

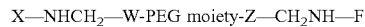

X—NHCH$_2$—W-PEG moiety-Z—CH$_2$NH—F wherein, —CH$_2$W— is a linking element linking the non-peptide polymer with X; and —Z—CH$_2$— is a linking element linking the non-peptide polymer with F. In addition, W and Z are absent or divalent functional groups such as alkylene, etc. The methylenes of —CH$_2$W— and —Z—CH$_2$— are derived from an aldehyde reactive group, and the nitrogen atoms of X—NH and NH—F are derived from the amino groups of the insulin analog and F, which were used in the linking reaction, respectively.

In the structure above, the PEG moiety may contain not only the structure —(CH$_2$CH$_2$O)$_n$—, but also an oxygen atom interposed between the linking element and —(CH$_2$CH$_2$O)$_n$—.

In the present invention, "immunoglobulin Fc region" refers to a region including the heavy chain constant region 2 (CH2) and/or the heavy chain constant region 3 (CH3), excluding the heavy chain and light chain variable regions of an immunoglobulin. The immunoglobulin Fc region may be one element that constitutes a moiety of the conjugate of the present invention.

The immunoglobulin Fc region may include a hinge region in the heavy chain constant region, but is not limited thereto. Additionally, the immunoglobulin Fc region of the present invention may be an extended Fc region including a part or the entirety of the heavy chain constant region 1 (CH1) and/or the light chain constant region 1 (CL1), excluding the heavy chain and the light chain variable regions of the immunoglobulin, as long as the immunoglobulin Fc region has an effect substantially the same as or improved compared to the native type. Additionally, the immunoglobulin Fc region of the present invention may be a region in which a fairly long part of the amino acid sequence corresponding to CH2 and/or CH3 is removed.

For example, the immunoglobulin Fc region of the present invention may be 1) a CH1 domain, a CH2 domain, a CH3 domain, and a CH4 domain; 2) a CH1 domain and a CH2 domain; 3) a CH1 domain and a CH3 domain; 4) a CH2 domain and a CH3 domain; 5) a combination between one or two or more domains among a CH1 domain, a CH2 domain, a CH3 domain, and a CH4 domain and an immunoglobulin hinge region (or a part of the hinge region); and 6) a dimer between each domain of the heavy chain constant region and the light chain constant region, but is not limited thereto.

Additionally, in an exemplary embodiment, the immunoglobulin Fc region may be in a dimeric form and one molecule of X may be covalently linked to one Fc region in a dimer form, where the immunoglobulin Fc and X may be linked to each other by a non-peptide polymer. Meanwhile, it is also possible that two molecules of X are each symmetrically linked to one Fc region in a dimer form. In particular, the immunoglobulin Fc and X can be linked to each other via a non-peptide linker, but are not limited to the examples described above.

Additionally, the immunoglobulin Fc region of the present invention not only includes a native amino acid sequence but also a sequence derivative thereof. An amino acid sequence derivative refers to an amino acid sequence which has a difference in at least one amino acid residue due to deletion, insertion, non-conservative or conservative substitution, or a combination thereof.

For example, the amino acid residues at positions 214 to 238, 297 to 299, 318 to 322, or 327 to 331, which are known to be in the conjugation of an immunoglobulin Fc, may be used as suitable sites for modification.

Additionally, various kinds of other derivatives may be prepared by removing the sites for forming a disulfide bond, removing a few amino acids at the N-terminus of a native Fc, inserting a methionine residue at the N-terminus of a native Fc, etc. Additionally, to remove effector functions, a complement-binding site, e.g., a C1q-binding site, may be removed or an antibody dependent cell mediated cytotoxicity (ADCC) site may be removed. The techniques for preparing these sequence derivatives of the immunoglobulin Fc region are disclosed in International Publication Nos. WO 97/34631, WO 96/32478, etc.

Amino acid exchanges in proteins and peptides which do not entirely alter the activity of the proteins or peptides are known in the art (H. Neurath, R. L. Hill, *The Proteins*, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly, in both directions. Depending on the case, the Fc region may be modified by phosphorylation, sulfation, acrylation, glycosylation, methylation, farnesylation, acetylation, amidation, etc.

The above-described Fc derivatives show a biological activity identical to that of the Fc region of the present invention and they may have improved structural stability against heat, pH, etc.

Further, the immunoglobulin Fc region may be obtained from native forms isolated in vivo from humans or animals such as cows, goats, pigs, mice, rabbits, hamsters, rats, guinea pigs, etc., or may be recombinants or derivatives thereof, obtained from transformed animal cells or microorganisms. Herein, the Fc region may be obtained from a native immunoglobulin by isolating a whole immunoglobulin from a living human or animal body and treating the isolated immunoglobulin with protease. When the whole immunoglobulin is treated with papain, it is cleaved into Fab and Fc regions, whereas when the whole immunoglobulin is treated with pepsin, it is cleaved into pF'c and F(ab)$_2$ fragments. Fc or pF'c can be isolated using size exclusion chromatography, etc. In a more specific embodiment, a human-derived Fc region is a recombinant immunoglobulin Fc region obtained from a microorganism.

In addition, the immunoglobulin Fc region may be in the form of natural glycans, increased or decreased glycans compared to the natural type, or in a deglycosylated form. The increase, decrease, or removal of the immunoglobulin Fc glycans may be achieved by conventional methods such as a chemical method, an enzymatic method, and a genetic engineering method using a microorganism. The immunoglobulin Fc region obtained by removal of glycans from the Fc region shows a significant decrease in binding affinity to the C1q part and a decrease or loss in antibody-dependent cytotoxicity or complement-dependent cytotoxicity, and thus it does not induce unnecessary immune responses in vivo. In this regard, an immunoglobulin Fc region in a deglycosylated or aglycosylated immunoglobulin Fc region may be a more suitable form to meet the original object of the present invention as a drug carrier.

As used herein, the term "deglycosylation" refers to enzymatically removing sugar moieties from an Fc region, and the term "aglycosylation" refers to an unglycosylated Fc region produced in prokaryotes, more specifically, *E. coli*.

Meanwhile, the immunoglobulin Fc region may be derived from humans or other animals including cows, goats, pigs, mice, rabbits, hamsters, rats, and guinea pigs. In a more specific embodiment, it is derived from humans.

In addition, the immunoglobulin (Ig) Fc region may be derived from IgG, IgA, IgD, IgE, IgM, or a combination or hybrid thereof. In a more specific embodiment, it is derived from IgG or IgM, which are among the most abundant proteins in human blood, and in an even more specific embodiment, it is derived from IgG, which is known to enhance the half-lives of ligand-binding proteins. In a yet even more specific embodiment, the immunoglobulin Fc region is an IgG4 Fc region, and in the most specific embodiment, the IgG4 Fc region is an aglycosylated Fc region derived from human IgG4, but is not limited thereto.

In particular, as used herein, the term "combination" means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

Another aspect of the present invention provides a polynucleotide encoding the conjugate, a vector including the polynucleotide, and a transformant including the polynucleotide or a vector including the polynucleotide.

The conjugate is the same as explained above.

The polynucleotide may be one that encodes a conjugate in the form of a fusion protein.

Additionally, the isolated polynucleotide encoding the conjugate includes, within the scope of the present invention, a polynucleotide sequence having a sequence identity to the corresponding sequence of 75% or higher, specifically 85% or higher, more specifically 90% or higher, and even more specifically 95% or higher.

The above description of the vector and transformant also applies to this embodiment.

Still another aspect of the present invention provides a method for preparing the conjugate.

The conjugate is as described above.

Specifically, the method may include the following steps:
(a) reacting a non-peptide polymer having two or more reactive end groups with one of an insulin analog and a carrier to prepare a non-peptide polymer, in which the insulin analog or carrier is attached to one end and the reactive end groups are attached to the other end; and
(b) reacting the non-peptide polymer prepared in step (a), in which the insulin analog or carrier is attached to one end and the reactive end groups are attached to the other end, with the other of a carrier or an insulin analog to prepare a conjugate in which the insulin analog and carrier are linked via the non-peptide polymer.

The non-peptide polymer, carrier, and insulin analog and linking constitutions thereof are all as described above.

Still another aspect of the present invention provides a composition including the conjugate.

The conjugate is as described above.

In the present invention, the composition may be a pharmaceutical composition. Specifically, the composition may be a pharmaceutical composition for preventing or treating an insulin-related disease. More specifically, the composition may be a pharmaceutical composition for preventing or treating diabetes.

As used herein, the term "insulin-related disease" refers to a disease that occurs or progresses due to low or no insulin bioactivity; and an example of the insulin-related disease may include diabetes, but is not particularly limited thereto.

As used herein, the term "prevention" refers to all activities that inhibit or delay an insulin-related disease by administering the above conjugate or composition containing the conjugate, and the term "treatment" refers to all activities that improve or advantageously change the symptoms of an insulin-related disease by administering the above conjugate or composition containing the conjugate.

A pharmaceutical composition containing the insulin analog conjugate according to the present invention may include a pharmaceutically acceptable carrier. Such a carrier may be non-naturally occurring.

As used herein, the term "pharmaceutically acceptable" refers to the properties of having a sufficient amount to exhibit a therapeutic effect and not causing adverse effects, and may be easily determined by a skilled person in the art based on the factors well known in the medical field, such as the kind of disease, age, body weight, health status, sex, drug sensitivity of a patient, administration route, administration method, administration frequency, duration of treatment, a drug(s) to be mixed or administered simultaneously, etc.

For oral administration, the pharmaceutically acceptable carrier may contain a binder, a lubricant, a disintegrator, an excipient, a solubilizer, a dispersing agent, a stabilizer, a suspending agent, a coloring agent, a perfume, etc. For injectable preparations, the pharmaceutically acceptable carrier may contain a buffering agent, a preservative, an analgesic, a solubilizer, an isotonic agent, and a stabilizer. For preparations for topical administration, the pharmaceutically acceptable carrier may contain a base, an excipient, a lubricant, a preservative, etc. The pharmaceutical composition of the present invention may be formulated into various dosage forms in combination with the aforementioned pharmaceutically acceptable carriers. For example, for oral administration, the pharmaceutical composition may be formulated into tablets, troches, capsules, elixirs, suspensions, syrups, or wafers. For injectable preparations, the pharmaceutical composition may be formulated into a single-dose ampule or multidose container. The pharmaceutical composition may also be formulated into solutions, suspensions, tablets, pills, capsules, and sustained-release preparations.

Meanwhile, examples of carriers, excipients, and diluents suitable for formulation may include lactose, dextrose, sucrose, sorbitol, mannitol, xylitol, erythritol, maltitol, starch, acacia, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oils, etc. Additionally, the pharmaceutical formulations may further contain a filler, an anti-coagulant, a lubricant, a humectant, a flavoring agent, an emulsifier, a preservative, etc.

As used herein, the term "administration" refers to introduction of a particular material to a patient by an appropriate manner, and the conjugate of the present invention may be administered by any of the common routes as long as the drug can arrive at a target tissue. For example, intraperitoneal, intravenous, intramuscular, subcutaneous, intradermal, oral, topical, intranasal, intrapulmonary, and intrarectal administration may be performed, but the administration route is not limited thereto. However, since peptides are digested upon oral administration, active ingredients of a composition for oral administration should be coated or formulated for protection against degradation in the stomach. Specifically, the present composition may be administered in an injectable form. Additionally, the pharmaceutical composition may be administered using a certain apparatus capable of transporting the active ingredients into a target cell.

Additionally, the pharmaceutical composition of the present invention may be determined by the types of the drug as an active component as well as by several related factors including the types of diseases to be treated, administration routes, age, sex, and body weight of a patient, and severity of the illness.

The total effective dose of the composition of the present invention may be administered to a patient in a single dose or may be administered for a long period of time in multiple doses according to a fractionated treatment protocol. The amount of active ingredient(s) contained in the pharmaceutical composition of the present invention may vary depending on the disease severity. Specifically, the total daily dose of the conjugate of the present invention may be about 0.0001 mg to 500 mg per 1 kg of body weight of a patient. However, the effective dose of the conjugate is determined considering various factors including patient's age, body weight, health conditions, sex, disease severity, diet, and excretion rate, in addition to administration route and treatment frequency of the pharmaceutical composition. In this regard, those skilled in the art may easily determine the effective dose suitable for the particular use of the pharmaceutical composition of the present invention. The pharmaceutical composition according to the present invention is not particularly limited to the formulation and administration route and mode, as long as it shows the effects of the present invention.

To achieve the present invention, still another aspect of the present invention provides a long-acting formulation with increased in vivo duration and/or stability compared to a conjugate of native insulin, including the insulin analog conjugate.

The insulin analog and the conjugate are as described above.

To achieve the present invention, still another aspect of the present invention provides a method for treating an insulin-related disease, comprising administering the insulin analog conjugate or the composition thereof to a subject in need thereof.

The insulin analog and the conjugate are as described above.

In an embodiment, the insulin-related disease is diabetes, but is not particularly limited thereto.

To achieve the present invention, still another aspect of the present invention provides a use of the insulin analog conjugate in the preparation of a medicament.

In an embodiment, the medicament is for preventing or treating an insulin-related disease, but the use is not particularly limited thereto.

In another embodiment, the medicament is for preventing or treating diabetes, but the use is not particularly limited thereto.

To achieve the present invention, still another aspect of the present invention provides a use of the insulin analog conjugate in the treatment of an insulin-related disease, specifically diabetes.

The insulin analog, the conjugate, and the insulin-related disease are as described above.

Hereinafter, the present invention will be described in more detail with reference to the following examples. However, these examples are provided for illustrative purposes only, and the scope of the present invention should not be limited thereto in any manner.

Example 1: Preparation of Single-Chain Insulin Analog Expression Vector

In order to prepare insulin analogs having a single modified amino acid in the A-chain or the B-chain, respectively, using the native insulin-expressing vector under possession as a template, forward and reverse oligonucleotides were synthesized (Table 2), and then PCR was performed to amplify each of the genes for the analogs.

The amino acid sequences modified in the A-chain or the B-chain and analog names are shown in Table 1 below. In Table 1, Analog 1 represents an analog in which the $14^{th}$ amino acid of the A-chain (i.e., tyrosine, Y) is substituted with histidine (H), and Analog 6 represents an analog in which the $16^{th}$ amino acid of the B-chain (i.e., tyrosine, Y) is substituted with glutamic acid (E).

TABLE 1

| Insulin Analog No. | Sequence Modification |
| --- | --- |
| Analog 1 | $A^{14}Y \rightarrow H$ |
| Analog 2 | $A^{14}Y \rightarrow K$ |
| Analog 3 | $A^{19}Y \rightarrow E$ |
| Analog 4 | $A^{19}Y \rightarrow S$ |
| Analog 5 | $A^{19}Y \rightarrow T$ |
| Analog 6 | $B^{16}Y \rightarrow E$ |
| Analog 7 | $B^{16}Y \rightarrow S$ |
| Analog 8 | $B^{16}Y \rightarrow T$ |
| Analog 9 | $A^{14}Y \rightarrow A$ |
| Analog 10 | $A^{14}Y \rightarrow D$ |
| Analog 11 | $B^{16}Y \rightarrow D$ |
| Analog 12 | $B^{25}F \rightarrow D$ |
| Analog 13 | $B^{25}F \rightarrow E$ |

Primers for insulin analog amplification are shown in Table 2 below.

TABLE 2

| Analog | Sequence | SEQ ID NO |
| --- | --- | --- |
| Analog 1 | 5' CAGCATCTGCTCCCTCCATCAGCTGGAGAACTAC 3' | 1 |
|  | 5' GTAGTTCTCCAGCTGATGGAGGGAGCAGATGCTG 3' | 2 |
| Analog 2 | 5' CAGCATCTGCTCCCTCAAGCAGCTGGAGAACTAC 3' | 3 |
|  | 5' GTAGTTCTCCAGCTGCTTGAGGGAGCAGATGCTG 3' | 4 |
| Analog 3 | 5' CTACCAGCTGGAGAACGAGTGCAACTGAGGATCC 3' | 5 |
|  | 5' GGATCCTCAGTTGCACTCGTTCTCCAGCTGGTAG 3' | 6 |
| Analog 4 | 5' CTACCAGCTGGAGAACTCCTGCAACTGAGGATCC 3' | 7 |
|  | 5' GGATCCTCAGTTGCAGGAGTTCTCCAGCTGGTAG 3' | 8 |
| Analog 5 | 5' CTACCAGCTGGAGAACACCTGCAACTGAGGATCC 3' | 9 |
|  | 5' GGATCCTCAGTTGCAGGTGTTCTCCAGCTGGTAG 3' | 10 |
| Analog 6 | 5' CTGGTGGAAGCTCTCGAGCTAGTGTGCGGGGAAC 3' | 11 |
|  | 5' GTTCCCCGCACACTAGCTCGAGAGCTTCCACCAG 3' | 12 |
| Analog 7 | 5' CTGGTGGAAGCTCTCTCCCTAGTGTGCGGGGAAC 3' | 13 |
|  | 5' GTTCCCCGCACACTAGGGAGAGAGCTTCCACCAG 3' | 14 |
| Analog 8 | 5' CTGGTGGAAGCTCTCACCCTAGTGTGCGGGGAAC 3' | 15 |
|  | 5' GTTCCCCGCACACTAGGGTGAGAGCTTCCACCAG 3' | 16 |
| Analog 9 | 5' CAGCATCTGCTCCCTCGCCCAGCTGGAGAACTAC 3' | 17 |
|  | 5' GTAGTTCTCCAGCTGGGCGAGGGAGCAGATGCTG 3' | 18 |
| Analog 10 | 5' CAGCATCTGCTCCCTCGACCAGCTGGAGAACTAC 3' | 19 |
|  | 5' GTAGTTCTCCAGCTGGTCGAGGGAGCAGATGCTG 3' | 20 |
| Analog 11 | 5' CTGGTGGAAGCTCTCGACCTAGTGTGCGGGGAAC 3' | 21 |
|  | 5' GTTCCCCGCACACTAGGTCGAGAGCTTCCACCAG 3' | 22 |
| Analog 12 | 5' GGGGAACGAGGCTTCGACTACACACCCAAGACC 3' | 23 |
|  | 5' GGTCTTGGGTGTGTAGTCGAAGCCTCGTTCCCC 3' | 24 |
| Analog 13 | 5' GGGGAACGAGGCTTCGAGTACACACCCAAGACC 3' | 25 |
|  | 5' GGTCTTGGGTGTGTACTCGAAGCCTCGTTCCCC 3' | 26 |

A PCR reaction for insulin analog amplification was performed under the conditions of 95° C. for 30 seconds, 55° C. for 30 seconds, and 68° C. for 6 minutes, for 18 repeated cycles. The insulin analog fragments obtained under the conditions were inserted into pET22b vector to be expressed as intracellular inclusion bodies, and the thus-obtained expression vectors were named as pET22b-insulin analogs 1 to 13. The expression vectors contained nucleic acids encoding amino acid sequences of insulin analogs 1 to 13 under the control of T7 promoter, and insulin analog proteins were expressed as inclusion bodies in host cells including the expression vectors.

DNA sequences and protein sequences of insulin analogs 1 to 13 are given in Table 3 below.

Each sequence modification was examined by DNA sequence analysis, and as a result, each of the insulin analogs was confirmed to have been modified in their sequences according to the intended purpose.

TABLE 3

| Analog | | Sequence | SEQ ID NO |
|---|---|---|---|
| Analog 1 | DNA | TTC GTT AAC CAA CAC TTG TGT GGC<br>TCA CAC CTG GTG GAA GCT CTC TAC<br>CTA GTG TGC GGG GAA CGA GGC TTC<br>TTC TAC ACA CCC AAG ACC CGC CGG<br>GAG GCA GAG GAC CTG CAG GTG<br>GGG CAG GTG GAG CTG GGC GGG<br>GGC CCT GGT GCA GGC AGC CTG CAG<br>CCC TTG GCC CTG GAG GGG TCC CTG<br>CAG AAG CGT GGC ATT GTG GAA CAA<br>TGC TGT ACC AGC ATC TGC TCC CTC<br>CAT CAG CTG GAG AAC TAC TGC AAC | 27 |
| | Protein | Phe Val Asn Gln His Leu Cys Gly Ser His<br>Leu Val Glu Ala Leu Tyr Leu Val Cys Gly<br>Glu Arg Gly Phe Phe Tyr Thr Pro Lys Thr<br>Arg Ara Glu Ala Glu Asp Leu Gln Val Gly<br>Gln Val Glu Leu Gly Gly Gly Pro Gly Ala<br>Gly Ser Leu Gln Pro Leu Ala Leu Gln Gly<br>Ser Leu Gln Lys Arg Gly Ile Val Glu Gln Cys<br>Cys Thr Ser Ile Cys Ser Leu His Gln Leu Gln<br>Asn Tyr Cys Asn | 28 |
| Analog 2 | DNA | TTC GTT AAC CAA CAC TTG TGT GGC<br>TCA CAC CTG GTG GAA GCT CTC TAC<br>CTA GTG TGC GGG GAA CGA GGC TTC<br>TTC TAC ACA CCC AAG ACC CGC CGG<br>GAG GCA GAG GAC CTG CAG GTG<br>GGG CAG GTT GAG CTG GGC GGG<br>GGC CCT GGT GCA GGC AGC CTG CAG<br>CCC TTG GCC CTG GAG GGG TCC CTG<br>CAG AAG CGT GGC ATT GTG GAA CAA<br>TGC TGT ACC AGC ATC TGC TCC CTC<br>AAG CAG CTG GAG AAC TAC TGC AAC | 29 |
| | Protein | Phe Val Asa Gln His Leu Cys Gly Ser His<br>Leu Val Gln Ala Leu Tyr Leu Val Cys Gly<br>Glu Arg Gly Phe Phe Tyr Thr Pro Lys Thr<br>Arg Arg Gln Ala Glu Asp Leu Gln Val Gly<br>Gln Val Gln Leu Gly Gly Gly Pro Gly Ala<br>Gly Ser Leu Gln Pro Leu Ala Leu Gln Gly<br>Ser Leu Gln Lys Arg Gly Ile Val Gln Gln Cys<br>Cys Thr See Ile Cys Ser Leu Lys Gln Leu Gln<br>Asn Tyr Cys Asn | 30 |
| Analog 3 | DNA | TTC GTT AAC CAA CAC TTG TGT GGC<br>TCA CAC CTG GTG GAA GCT CTC TAC<br>CTA GTG TGC GGG GAA CGA GGC TTC<br>TTC TAC ACA CCC AAG ACC CGC CGG<br>GAG GCA GAG GAC CTG CAG GTG<br>GGG CAG GTG GAG CTG GGC GGG<br>GGC CCT GGT GCA GGC AGC CTG CAG<br>CCC TTG GCC CTG GAG GGG TCC CTG<br>CAG AAG CGT GGC ATT GTG GAA CAA<br>TGC TGT ACC AGC ATC TGC TCC CTC<br>TAC CAG CTG GAG AAC GAG TGC AAC | 31 |
| | Protein | Phe Val Asn Gln His Leu Cys Gly Ser His<br>Leu Val Glu Ala Leu Tyr Leu Val Cys Gly<br>Glu Arg Gly Phe Phe Tyr Thr Pro Lys Thr<br>Arg Arg Gln Ala Glu Asp Leu Gln Val Gly<br>Gln Val Glu Leu Gly Gly Gly Pro Gly Ala<br>Gly Ser Leu Gln Pro Leu Ala Leu Gln Gly<br>Ser Leu Gln Lys Arg Gly Ile Val Glu Gln Cys<br>Cys Thr Ser Ile Cys Ser Leu Tyr Gln Leu Glu<br>Asn Glu Cys Asn | 32 |

TABLE 3-continued

| Analog | | Sequence | SEQ ID NO |
|---|---|---|---|
| Analog 4 | DNA | TTC GTT AAC CAA CAC TTG TGT GGC<br>TCA CAC CTG GTG GAA GCT CTC TAC<br>CTA GTG TGC GGG GAA CGA GGC TTC<br>TTC TAC ACA CCC AAG ACC CGC CGG<br>GAG GCA GAG GAC CTG CAG GTG<br>GGG CAG GTG GAG CTG GGC GGG<br>GGC CCT GGT GCA GGC AGC CTG CAG<br>CCC TTG GCC CTG GAG GGG TCC CTG<br>CAG AAG CGT GGC ATT GTG GAA CAA<br>TGC TGT ACC AGC ATC TGC TCC CTC<br>TAC CAG CTG GAG AAC TCC TGC AAC | 33 |
| | Protein | Phe Val Asn Gln His Leu Cys Gly Ser His<br>Leu Val Gln Ala Leu Tyr Leu Val Cys Gly<br>Glu Arg Gly Phe Phe Tyr Thr Pro Lys Thr<br>Arg Arg Glu Ala Glu Asp Leu Gln Val Gly<br>Gln Val Glu Leu Gly Gly Gly Pro Gly Ala<br>Gly Ser Leu Gln Pro Leu Ala Leu Gln Gly<br>Ser Leu Gln Lys Arg Gly Ile Val Glu Gln Cys<br>Cys Thr Ser Ile Cys Ser Leu Tyr Gln Leu Glu<br>Asn Ser Cys Asn | 34 |
| Analog 5 | DNA | TTC GTT AAC CAA CAC TTG TGT GGC<br>TCA CAC CTG GTG GAA GCT CTC TAC<br>CTA GTG TGC GGG GAA CGA GGC TTC<br>TTC TAC ACA CCC AAG ACC CGC CGG<br>GAG GCA GAG GAC CTG CAG GTG<br>GGG CAG GTG GAG CTG GGC GGG<br>GGC CCT GGT GCA GGC AGC CTG CAG<br>CCC TTG GCC CTG GAG GGG TCC CTG<br>CAG AAG CGT GGC ATT GTG GAA CAA<br>TGC TGT ACC AGC ATC TGC TCC CTC<br>TAC CAG CTG GAG AAC ACC TGC AAC | 35 |
| | Protein | Phe Val Asn Gln His Leu Cys Gly Ser His<br>Leu Val Glu Ala Leu Tyr Leu Val Cys Gly<br>Gln Arg Gly Phe Phe Tyr Thr Pro Lys Thr<br>Arg Arg Gln Ala Gln Asp Leu Gln Val Gly<br>Gln Val Glu Leu Gly Gly Gly Pro Gly Ala<br>Gly Ser Leu Gln Pro Leu Ala Leu Glu Gly<br>Ser Leu Gln Lys Arg Gly Ile Val Glu Gln Cys<br>Cys Thr Ser Ile Cys Ser Leu Tyr Gln Leu Gln<br>Asn Thr Cys Asn | 36 |
| Analog 6 | DNA | TTC GTT AAC CAA CAC TTG TGT GGC<br>TCA CAC CTG GTG GAA GCT CTC GAG<br>CTA GTG TGC GGG GAA CGA GGC TTC<br>TTC TAC ACA CCC AAG ACC CGC CGG<br>GAG GCA GAG GAC CTG CAG GTG<br>GGG CAG GTG GAG CTG GGC GGG<br>GGC CCT GGT GCA GGC AGC CTG CAG<br>CCC TTG GCC CTG GAG GGG TCC CTG<br>CAG AAG CGT GGC ATT GTG GAA CAA<br>TGC TGT ACC AGC ATC TGC TCC CTC<br>TAC CAG CTG GAG AAC TAC TGC AAC | 37 |
| | Protein | Phe Val Asn Gln His Leu Cys Gly Ser His<br>Leu Val Glu Ala Leu Glu Leu Val Cys Gly<br>Glu Arg Gly Phe Phe Tyr Thr Pro Lys Thr<br>Arg Arg Gln Ala Glu Asp Leu Gln Val Gly<br>Gln Val Glu Leu Gly Gly Gly Pro Gly Ala<br>Gly Ser Leu Gln Pro Leu Ala Leu Gln Gly<br>Ser Leu Gln Lys Arg Gly Ile Val Glu Gln Cys<br>Cys Thr Ser Ile Cys Ser Leu Tyr Gln Leu Gln<br>Asn Tyr Cys Asn | 38 |
| Analog 7 | DNA | TTC GTT AAC CAA CAC TTG TGT GGC<br>TCA CAC CTG GTG GAA GCT CTC TCC<br>CTA GTG TGC GGG GAA CGA GGC TTC<br>TTC TAC ACA CCC AAG ACC CGC CGG<br>GAG GCA GAG GAC CTG CAG GTG<br>GGG CAG GTG GAG CTG GGC GGG<br>GGC CCT GGT GCA GGC AGC CTG CAG<br>CCC TTG GCC CTG GAG GGG TCC CTG<br>CAG AAG CGT GGC ATT GTG GAA CAA<br>TGC TGT ACC AGC ATC TGC TCC CTC<br>TAC CAG CTG GAG AAC TAC TGC AAC | 39 |
| | Protein | Phe Val Asn Gln His Leu Cys Gly Ser His<br>Leu Val Glu Ala Leu Ser Leu Val Cys Gly<br>Gln Arg Gly Phe Phe Tyr Thr Pro Lys Thr | 40 |

TABLE 3-continued

| Analog | | Sequence | SEQ ID NO |
|---|---|---|---|
| | | Arg Ara Gln Ala Glu Asp Leu Gln Val Gly | |
| | | Gln Val Glu Leu Gly Gly Gly Pro Gly Ala | |
| | | Gly Ser Leu Gln Pro Leu Ala Leu Glu Gly | |
| | | Ser Leu Gln Lys Arg Gly Ile Val Glu Gln Cys | |
| | | Cys Thr Ser Ile Cys Ser Leu Tyr Gln Leu Gln | |
| | | Asn Tyr Cys Asn | |
| Analog 8 | DNA | TTC GTT AAC CAA CAC TTG TGT GGC | 41 |
| | | TCA CAC CTG GTG GAA GCT CTC ACC | |
| | | CTA GTG TGC GGG GAA CGA GGC TTC | |
| | | TTC TAC ACA CCC AAG ACC CGC CGG | |
| | | GAG GCA GAG GAC CTG CAG GTG | |
| | | GGG CAG GTG GAG CTG GGC GGG | |
| | | GGC CCT GGT GCA GGC AGC CTG CAG | |
| | | CCC TTG GCC CTG GAG GGG TCC CTG | |
| | | CAG AAG CGT GGC ATT GTG GAA CAA | |
| | | TGC TGT ACC AGC ATC TGC TCC CTC | |
| | | CAC CAG CTG GAG AAC TAC TGC AAC | |
| | Protein | Phe Val Asn Gln His Leu Cys Gly Ser His | 42 |
| | | Leu Val Gln Ala Leu Thr Leu Val Cys Gly | |
| | | Glu Ara Gly Phe Phe Tyr Thr Pro Lys Thr | |
| | | Arg Arg Glu Ala Glu Asp Leu Gln Val Gly | |
| | | Gln Val Glu Leu Gly Gly Gly Pro Gly Ala | |
| | | Gly Ser Leu Gln Pro Leu Ala Leu Gln Gly | |
| | | Ser Leu Gln Lys Arg Gly Ile Val Glu Gln Cys | |
| | | Cys Thr Ser Ile Cys Ser Leu Tyr Gln Leu Glu | |
| | | Asn Tyr Cys Asn | |
| Analog 9 | DNA | TTC GTT AAC CAA CAC TTG TGT GGC | 43 |
| | | TCA CAC CTG GTG GAA GCT CTC TAC | |
| | | CTA GTG TGC GGG GAA CGA GGC TTC | |
| | | TTC TAC ACA CCC AAG ACC CGC CGG | |
| | | GAG GCA GAG GAC CAA CAG GTG | |
| | | GGG CAG GTG GAG CTG GGC GGG | |
| | | GGC CCT GGT GCA GGC AGC CTG CAG | |
| | | CCC TTG GCC CTG GAG GGG TCC CTG | |
| | | CAG AAG CGT GGC ATT GTG GAA CAA | |
| | | TGC TGT ACC AGC ATC TGC TCC CTC | |
| | | GCC CAG CTG GAG AAC TAC TGC AAC | |
| | Protein | Phe Val Asn Gln His Leu Cys Gly Ser His | 44 |
| | | Leu Val Glu Ala Leu Tyr Leu Val Cys Gly | |
| | | Glu Arg Gly Phe Phe Tyr Thr Pro Lys Thr | |
| | | Arg Ara Glu Ala Glu Asp Leu Gln Val Gly | |
| | | Gln Val Glu Leu Gly Gly Gly Pro Gly Ala | |
| | | Gly Ser Leu Gln Pro Leu Ala Leu Gln Gly | |
| | | Ser Leu Gln Lys Arg Gly Ile Val Glu Gln Cys | |
| | | Cys Thr Ser Ile Cys Ser Leu Ala Gln Leu Glu | |
| | | Asn Tyr Cys Asn | |
| Analog 10 | DNA | TTC GTT AAC CAA CAC TTG TGT GGC | 45 |
| | | TCA CAC CTG GTG GAA CCT CTC TAC | |
| | | CTA GTG TGC GGG GAA CGA GGC TTC | |
| | | TTC TAC ACA CCC AAG ACC CCC CCC | |
| | | GAG GCA GAG GAC CTG CAG GTG | |
| | | GGG CAG GTG GAG CTG GGC GGG | |
| | | GGC CCT GGT GCA GGC AGC CTG CAG | |
| | | CCC TTG GCC CTG GAGGGG TCC CTG | |
| | | CAG AAG CGT GGC ATT GTG GAA CAA | |
| | | TGC TGT ACG AGC ATC TCC TCC CTC | |
| | | GAC CAG CTG GAG AAC TA TCC AAC | |
| | Protein | Phe Val Asn Gln His Leu Cys Gly Ser His | 46 |
| | | Leu Val Gln Ala Leu Tyr Leu Val Cys Gly | |
| | | Glu Ara Gly Phe Phe Tyr Thr Pro Lys Thr | |
| | | Arg Arg Glu Ala Glu Asp Leu Gln Val Gly | |
| | | Gln Val Gln Leu Gly Gly Gly Pro Gly Ala | |
| | | Gly Ser Leu Gln Pro Leu Ala Leu Gln Gly | |
| | | Ser Leu Gln Lys Arg Gly Ile Val Gln Gln Cys | |
| | | Cys Thr Ser Ile Cys Ser Leu Asp Gln Leu | |
| | | Glu Asn Tyr Cys Asn | |
| Analog 11 | DNA | TTC GTT AAC CAA CAC TTG TGT GGC | 47 |
| | | TCA CAC CTG GTG GAA GCT CTC GAC | |
| | | CTA GTG TGC GGG GAA CGA GGC TTC | |
| | | TTC TAC ACA CCC AAG ACC CGC CGG | |
| | | GAG GCA GAG GAC CTG CAG GTG | |
| | | GGG CAG GTG GAG CTG GGC GGG | |
| | | GGC CCT GGT GCA GGC AGC CTG CAG | |

TABLE 3-continued

| Analog | | Sequence | SEQ ID NO |
|---|---|---|---|
| | | CCC TTG GCC CTG GAG GGG TCC CTG<br>CAG AAG CGT GGC ATT GTG GAA CAA<br>TGC TGT ACC AGC ATC TGC TCC CTC<br>TAC CAG CTG GAG AAC TAC TGC AAC | |
| | Protein | Phe Val Asn Gln His Leu Cys Gly Ser His<br>Leu Val Glu Ala Leu Asp Leu Val Cys Gly<br>Glu Arg Gly Phe Phe Tyr Thr Pro Lys Thr<br>Arg Arg Glu Ala Glu Asp Leu Gln Val Gly<br>Gln Val Glu Leu Gly Gly Gly Pro Gly Ala<br>Gly Ser Leu Gln Pro Leu Ala Leu Gln Gly<br>Ser Leu Gln Lys Arg Gly Ile Val Glu Gln Cys<br>Cys Thr Ser Ile Cys Ser Leu Tyr Gln Leu Glu<br>Asn Tyr Cys Asn | 48 |
| Analog 12 | DNA | TTC GTT AAC CAA CAC TTG TGT GGC<br>TCA CAC CTG GTG GAA GCT CTC TAC<br>CTA GTG TGC GGG GAA CGA GGC TTC<br>GAC TAC ACA CCC AAG ACC CGC CGG<br>GAG GCA GAG GAC CTG CAG GTG<br>GGG CAG GTG GAG CTG GGC GGG<br>GGC CCT GGT GCA GGC AGC CTG CAG<br>CCC TTG GCC CTG GAG GGG TCC CTG<br>CAG AAG CGT GGC ATT GTG GAA CAA<br>TGC TGT ACC AGC ATC TGC TCC CTC<br>TAC CAG CTG GAG AAC TAC TGC AAC | 49 |
| | Protein | Phe Val Asn Gln His Leu Cys Gly Ser His<br>Leu Val Glu Ala Leu Tyr Leu Val Cys Gly<br>Glu Arg Gly Phe Asp Tyr Thr Pro Lys Thr<br>Arg Arg Glu Ala Glu Asp Leu Gln Val Gly<br>Gln Val Glu Leu Gly Gly Gly Pro Gly Ala<br>Gly Ser Leu Gln Pro Leu Ala Leu Glu Gly<br>Ser Leu Gln Lys Arg Gly Ile Val Glu Gln Cys<br>Cys Thr Ser Ile Cys Ser Leu Tyr Gln Leu Glu<br>Asn Tyr Cys Asn | 50 |
| Analog 13 | DNA | TTC GTT AAC CAA CAC TTG TGT GGC<br>TCA CAC CTG GTG GAA GCT CTC TAC<br>CTA GTG TGC GGG GAA CGA GGC TTC<br>GAG TAC ACA CCC AAG ACC CGC CGG<br>GAG GCA GAG GAC CTG CAG GTG<br>GGG CAG GTG GAG CTG GGC GGG<br>GGC CCT GGT GCA GGC AGC CTG CAG<br>CCC TTG GCC CTG GAG GGG TCC CTG<br>CAG AAG CGT GGC ATT GTG GAA CAA<br>TGC TGT ACC AGC ATC TGC TCC CTC<br>TAC CAG CTG GAG AAC TAC TGC AAC | 51 |
| | Protein | Phe Val Asn Gln His Leu Cys Gly Ser His<br>Leu Val Glu Ala Leu Tyr Leu Val Cys Gly<br>Gln Arg Gly Phe Glu Tyr Thr Pro Lys Thr<br>Arg Arg Gln Ala Glu Asp Leu Gln Val Gly<br>Gln Val Gln Leu Gly Gly Gly Pro Gly Ala<br>Gly Ser Leu Gln Pro Leu Ala Leu Gln Gly<br>Ser Leu Gln Lys Arg Gly Ile Val Glu Gln Cys<br>Cys Thr Ser Ile Cys Ser Leu Tyr Gln Leu Gln<br>Asn Tyr Cys Asn | 52 |

Example 2: Expression of Recombinant Insulin Analog Fusion Peptides

Expressions of recombinant insulin analogs were performed under the control of T7 promoter. *E. coli* BL21-DE3 (*E. coli* B F-dcm ompT hsdS(rB-mB-) gal λDE3; Novagen) was transformed with each of the recombinant insulin analog-expressing vectors. Transformation was performed in accordance with the recommended protocol (Novagen). Single colonies transformed with each recombinant expression vector were collected, inoculated in 2× Luria Broth (LB) containing ampicillin (50 µg/mL), and cultured at 37° C. for 15 hours. The recombinant strain culture broth and 2×LB medium containing 30% glycerol were mixed in a ratio of 1:1 (v/v), 1 mL each of the mixture was dispensed to a cryotube and stored at −140° C., which was used as a cell stock for producing the recombinant fusion protein.

To express the recombinant insulin analogs, one vial of each cell stock was thawed and inoculated into 500 mL of 2× Luria broth, and cultured with shaking at 37° C. for 14 hours to 16 hours. The cultivation was terminated when OD600 reached 5.0 or higher and the culture broth was used as a seed culture broth. The seed culture broth was inoculated to 17 L of fermentation medium using a 50 L fermentor (MSJ-U2, B. E. MARUBISHI, Japan), and initial bath fermentation was started. The culture conditions were maintained at a temperature of 37° C., an air flow rate of 20 L/min (1 vvm), an agitation speed of 500 rpm, and at pH 6.70 using a 30% ammonia solution. Fermentation was performed in fed-batch mode by adding a feeding solution, when nutrients were depleted in the culture broth. Growth of the strain was monitored by OD value. IPTG was introduced to a final concentration of 500 µM, when the OD value reached 100 or higher. After introduction, the cultivation was progressed further for about 23 hours to 25 hours. Upon termination of the cultivation, the recombinant strains were harvested by centrifugation and stored at −80° C. until use.

Example 3: Recovery and Refolding of Recombinant Insulin Analogs

In order to change the recombinant insulin analogs expressed in Example 2 into soluble forms, cells were disrupted followed by refolding. The cell pellet (100 g; wet weight) was resuspended in 1 L lysis buffer (50 mM Tris-HCl (pH 9.0), 1 mM EDTA (pH 8.0), 0.2 M NaCl, and 0.5% Triton X-100). The cells were disrupted using a microfluidizer (Microfluidic Inc. Model M-110EH-30) at an operating pressure of 15,000 psi. The thus-disrupted cell lysate was centrifuged at 7,000 rpm at a temperature of 4° C. to 8° C. for 20 minutes. The supernatant was discarded and the pellet was resuspended in 3 L washing buffer (0.5% Triton X-100 and 50 mM Tris-HCl (pH 8.0), 0.2 M NaCl, and 1 mM EDTA). After centrifugation at 7,000 rpm at a temperature of 4° C. to 8° C. for 20 minutes, the cell pellet was resuspended in distilled water, followed by centrifugation in the same manner. The thus-obtained pellet was resuspended in buffer (1 M L-glycine, 3.78 g L-cysteine-HCl, pH 10.6) and stirred at room temperature for 1 hour. To recover the recombinant insulin analog thus resuspended. 8 M urea was added thereto and stirred for 3 hours to 5 hours. For refolding of the solubilized recombinant proinsulin analogs, centrifugation was carried out at 7,000 rpm at a temperature of 4° C. to 8° C. for 30 minutes, the supernatant was collected, and treated with 15 mM L-cysteine-HCl, i.e., a reducing agent, for one hour. A predetermined volume of distilled water was added thereto using a peristaltic pump and stirred at a temperature of 4° C. to 8° C. for at least 12 hours.

Example 4: Cation Exchange Chromatography Purification

The sample, upon completion of refolding, was loaded onto an equilibrated SP FF (GE healthcare) column equilibrated with 20 mM sodium citrate (pH 2.0) buffer containing 45% ethanol, and then the insulin analog proteins were eluted in 10 column volumes with a linear gradient from 0% to 100% using a 20 mM sodium citrate (pH 2.0) buffer containing 0.5 M potassium chloride and 45% ethanol.

Example 5: Treatment with Trypsin and Carboxypeptidase B

Salts were removed from the eluted samples using an ultrafiltration membrane, followed by replacement of a buffer solution (10 mM Tris-HCl, pH 8.0). The thus-obtained sample protein was treated with trypsin corresponding to a molar ratio of about 30,000 relative to the protein amount of the sample and carboxypeptidase B corresponding to a molar ratio of about 3,000 molar ratio relative to the protein amount of the sample and stirred at a temperature of 4° C. to 8° C. for at least 16 hours.

Example 6: Cation Exchange Chromatography Purification

The sample, upon completion of the reaction, was reloaded onto an equilibrated SP HP (GE healthcare) column equilibrated with 20 mM sodium citrate (pH 2.0) buffer containing 45% ethanol, and the insulin analog proteins were eluted in 10 column volumes with a linear gradient from 0% to 100% using a 20 mM sodium citrate (pH 2.0) buffer containing 0.5 M potassium chloride and 45% ethanol.

Example 7: Reversed Phase Chromatography Purification

For the pure separation of the pure insulin analog from the sample obtained in Example 6, it was loaded onto the reversed phase chromatography Source30RPC (GE healthcare, USA), which was equilibrated with sodium phosphate and isopropanol, and the insulin analog proteins were eluted with a linear gradient using a buffer containing sodium phosphate and isopropanol.

The thus-purified insulin analogs were analyzed by protein electrophoresis (SDS-PAGE, FIG. 1) and HPLC, and among them, the purity results of representative insulin analogs 9, 10, 11, and 12 are shown in FIGS. 2a-2d.

Example 8: Preparation of Long-Acting Insulin Analog Conjugate

The conjugates of the insulin analogs prepared in Examples 1 to 7 were prepared by the following method.

The long-acting conjugate of analog 10 was representatively prepared as follows.

To PEGylate 3.4K propion-ALD(2) PEG (PEG (3.4 kDa) having a propionaldehyde group at each of both ends; NOF Inc., USA) at the N-terminus of the B-chain of insulin analog 10, the concentration (5 mg/mL) of insulin analog 10, the molar ratio of which with PEG is 1:4, was reacted at 4° C. for about 2 hours. Herein, the reaction was carried out by adding a reducing agent of 3 mM sodium cyanoborohydride ($NaCNBH_3$) in a mixed solvent of a 50 mM sodium citrate buffer (pH 5.0) and 45% isopropanol. The reaction solution was purified by an SP-HP (GE Healthcare) column which uses a KCl concentration gradient and a buffer containing sodium citrate (pH 3.0) and 45% EtOH.

In order to link PEG, to which the insulin analog is attached, with the N-terminus of the immunoglobulin Fc fragment, the molar ratio of the purified mono-PEGylated insulin analog and the immunoglobulin Fc fragment was established to be 1:1.2, and the reaction was carried out at 25° C. for 15 hours while setting a total protein concentration to be 20 mg/mL. Herein, the reaction solution, in which 20 mM sodium cyanoborohydride as a reducing agent and sodium chloride were added to a 100 mM HEPES buffer (pH 8.2), was used.

After completion of the reaction, the reaction solution was applied to a Q-HP column (GE, USA) using a Tris-HCl buffer (pH 7.5) and a NaCl concentration gradient, and was applied to Source 15ISO (GE, USA) using ammonium sulfate and a concentration gradient of Tris-HCl (pH 7.5), and thereby the insulin analog 10-3.4K PEG-immunoglobulin Fc conjugate was purified.

Comparative Example: Preparation of Long-Acting Conjugate of Native Insulin

To PEGylate 3.4K propion-ALD(2) PEG (PEG (3.4 kDa) having a propionaldehyde group at each of both ends; NOF Inc., USA) at the N-terminus of the B-chain of native insulin (Biocon Inc., India), the pegylation reaction was performed and the mono-PEGylated native insulin was purified by the purification column as in Example 8.

In order to link PEG, to which the native insulin is attached, with the N-terminus of the immunoglobulin Fc fragment, the reaction conditions and purification column as described in Example 8 were applied to the purified mono-PEGylated native insulin and the immunoglobulin Fc fragment, and thereby the native insulin-3.4K PEG-immunoglobulin Fc conjugate was prepared.

Experimental Example 1: Comparison of Binding Affinity of Insulin Analogs for Insulin Receptors For the measurement of binding affinity of insulin analogs to insulin receptors, the analysis was performed by scintillation proximity assay (SPA). First, to obtain a cell membrane expressing insulin receptor B isoform, a CHO cell line in which the insulin receptor B isoform is overexpressed was prepared by using the CHO cell line and the transfection method using lipofectamine (Life Technology, USA). The prepared cell line was then homogenized with a homogenizer (Wheaton, USA), and the cell membrane was separated using a sucrose cushion method. The obtained cell membrane of the CHO cell line, in which the human native insulin receptor B isoform is expressed, and PVT SPA beads were added into 96-well pico plates (PerkinElmer, Model No. 6005162, USA). In addition, as a competitor, human insulin or each of the insulin analogs diluted in more than 10 different concentrations (50 mM Tris-HCl pH 7.8, 150 mM NaCl, 0.1% BSA) was added together with radioisotope $I^{125}$-tagged human native insulin (PerkinElmer, Model No. NEX-420, USA), as a detector ligand, and was allowed to react competitively at room temperature for 4 hours. Four hours thereafter, the binding affinity to insulin receptors was measured using a beta counter (PerkinElmer, Model No. C9904V1, USA). The values of each material measured by the beta counter were calculated in $IC_{50}$ using the GraphPad Prism 6 software, and the percentage of insulin receptor $IC_{50}$ of the insulin analog was digitized as the relative binding affinity against the human insulin to the insulin receptor.

As a result, compared to the human insulin, the binding affinity to the insulin receptors was shown to be 90% for insulin analog 1; 95% for insulin analog 2; 1.0% for insulin analog 3; <0.1% for insulin analog 4; 20% for insulin analog 6; 8.5% for insulin analog 7; 79% for insulin analog 9, 79% for insulin analog 10; 24% for insulin analog 11; <0.1% for insulin analog, 12; and <0.1% for insulin analog 13 (Table 4). Accordingly, the insulin analogs of the present invention were observed to have reduced binding affinity to insulin receptors compared to the native insulin.

TABLE 4

| Material Name | | Binding Affinity to Insulin Receptors (vs. Human Insulin) |
| --- | --- | --- |
| Insulin analog | insulin analog 1 | 90% |
| | insulin analog 2 | 95% |
| | insulin analog 3 | 1.0% |
| | insulin analog 4 | <0.1% |
| | insulin analog 6 | 20% |
| | insulin analog 7 | 8.5% |
| | insulin analog 9 | 79% |
| | insulin analog 10 | 79% |
| | insulin analog 11 | 24% |
| | insulin analog 12 | <0.1% |
| | insulin analog 13 | <0.1% |

Experimental Example 2: Confirmation of Receptor Binding Affinity of Long-Acting Insulin Analog Conjugate The binding affinity to the insulin receptor and IGF-1 receptor of the long-acting insulin analog was confirmed by the method described in Experimental Example 1 above.

As a result, compared with native human insulin, the binding affinity to the insulin receptor was 2.4±0.4% for the native insulin-PEG-immunoglobulin Fc conjugate, and was 1.3±0.2% for the insulin analog 10-PEG-immunoglobulin Fc conjugate. In addition, compared with human native IGF-1, the binding affinity to the IGF-1 receptor was less than 1% for both the native insulin-PEG-immunoglobulin Fc conjugate and the insulin analog 10-PEG-immunoglobulin Fc conjugate. Accordingly, it was confirmed that the insulin analog 10-PEG-immunoglobulin Fc conjugate had reduced binding affinity to the insulin receptor as compared with the native insulin-PEG-immunoglobulin Fc conjugate, and that both substances had reduced binding affinity to the IGF-1 receptor due to the conjugation of PEG and immunoglobulin Fc.

TABLE 5

| In vitro conjugation | | Native insulin-PEG-immunoglobulin Fc conjugate | Insulin analog 10-PEG-immunoglobulin Fc conjugate |
| --- | --- | --- | --- |
| Receptor binding affinity (% vs. insulin, SPA method) | IR-B conjugation | 2.4 ± 0.4 | 1.3 ± 0.2 |
| | IGF-1R conjugation[1] | <1% | <1% |

[1]Since the dose-response curve did not reach saturation at the highest concentration, the exact value was not measured.

Experimental Example 3: Pharmacokinetic Analysis of Long-Acting Insulin Analog Conjugate In order to confirm the pharmacokinetics of the long-acting insulin analog conjugate, a comparison study of blood concentration levels over time was carried in normal rats (SD rats, male, 6 weeks old), normal mice, and dogs, which adapted to the laboratory over a certain period of time.

The native insulin-PEG-immunoglobulin Fc conjugate and the insulin analog 10-PEG-immunoglobulin Fc conjugate were each subcutaneously administered to mice at 43.05 nmol/kg and to rats at 65.1 nmol/kg in a single dose. Thereafter, the blood samples were collected at 0, 1, 4, 8, 24, 48, 72, 96, 120, 144, and 168 hours. In addition, the native insulin-PEG-immunoglobulin Fc conjugate and the insulin analog 10-PEG-immunoglobulin Fc conjugate were each subcutaneously administered to dogs at 6.3 nmol/kg in a single dose. Thereafter, the blood samples were collected at 0, 1, 4, 8, 24, 48, 72, 96, 120, 144, 168, 192, 216, and 240 hours.

At each time point, blood concentrations of the native insulin-PEG-immunoglobulin Fc conjugate and insulin analog 10-PEG-immunoglobulin Fc conjugate were measured by enzyme linked immunosorbent assay (ELISA), and Insulin ELISA (ALPCO, USA) was used as a kit. However, as a detection antibody, the mouse anti-human IgG4 HRP conjugate (Alpha Diagnostic Intl, Inc, USA) was used.

As a result, compared to the native insulin-PEG-immunoglobulin Fc conjugate, the half-life of the insulin analog 10-PEG-immunoglobulin Fc conjugate was increased by 1.9-fold, 1.2-fold, and 1.6-fold in the mice, rats, and dogs, respectively, and MRT was increased by 2.5-fold, 1.9-fold, and 2.0-fold, respectively. Accordingly, it was confirmed that the insulin analog-PEG-immunoglobulin Fc conjugate showed an increased durability in the blood compared to the native insulin-PEG-immunoglobulin Fc conjugate.

TABLE 6

| Test materials | | Native insulin-PEG-immunoglobulin Fc conjugate | Insulin analog 10-PEG-immunoglobulin Fc conjugate |
|---|---|---|---|
| Mice (43.05 nmol/kg sc, n = 3) | $t_{1/2}$ (hr) | 15.4 | 29.7 |
| Rats (65.1 nmol/kg, sc, n = 3) | $t_{1/2}$ (hr) | 18.5 ± 1.4 | 22.8 ± 2.2 |
| Dogs (6.3 nmol/kg, sc, n = 3) | $t_{1/2}$ (hr) | 28.8 ± 2.0 | 44.9 ± 7.1 |

Experimental Example 4: Determination of the Glucose Level-Lowering Effect of Long-Acting Insulin Analog Conjugate In order to confirm the pharmacodynamics of the long-acting insulin analog conjugate in a type-2 diabetic model, a high-fat diet (60% fat) was fed to normal rats (SD rats, male, 7 weeks old) for 2 weeks, and STZ capable of destroying pancreatic beta cells was administered at a dose of 30 mg/kg twice a week to manufacture a type-2 diabetic model (hereinafter referred to as DIO/STZ rats). The high-fat diet was continuously fed to the manufactured model to maintain continuous diabetes.

The native insulin-PEG-immunoglobulin Fc conjugate and the insulin analog 10-PEG-immunoglobulin Fc conjugate were subcutaneously administered to the DIO/STZ rats at 12.1 nmol/kg and 8.09 nmol/kg, respectively, and the administration was repeatedly performed at intervals of 3 days. In order to determine the effect of lowering in vivo blood glucose levels by the administrations of the native insulin-PEG-immunoglobulin Fc conjugate and the insulin analog 10-PEG-immunoglobulin Fc conjugate, the blood samples were collected from caudal veins on days 0, 1, 3, 6, 7, 9, 10, 12, 13, 15, 16, 21, 22, 24, 25, 27, and 28 of the administration, and the in vivo blood glucose levels were determined using an in vivo blood glucose meter (One-Touch® Ultra®, LifeScan, Inc., USA).

As a result, it was confirmed that the insulin analog 10-PEG-immunoglobulin Fc conjugate had an equivalent effect of lowering in vivo blood glucose levels compared to the native insulin-PEG-immunoglobulin Fc conjugate, even when the conjugate was administered at a dose of 50% to the DIO/STZ rats. Based on the result above, it was thus confirmed that the improved in vivo blood durability of the insulin analog 10-PEG-immunoglobulin Fc conjugate of the present invention could continuously maintain the excellent effect of lowering in vivo blood glucose levels even with a small dose thereof compared to the native insulin-PEG-immunoglobulin Fc conjugate.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A conjugate of Formula 1:

X-L$_a$-F    [Formula 1]

wherein in Formula 1,
X is an insulin analog consisting of an A-chain of SEQ ID NO: 55 of Formula 2 and a B-chain of SEQ ID NO: 56 of Formula 3 with the proviso that the peptide where the A-chain coincides with SEQ ID NO: 53 while the B-chain also coincides with SEQ ID NO: 54 is excluded;
L is a linker;
a is 0 or a natural number, with the proviso that when a is 2 or greater, each L is independent from each other;
F is a substance capable of increasing the half-life of X; and
X, L, and F are linked to each other by a covalent bond in the order of Formula 1:

[Formula 2]
(SEQ ID NO: 55)
Xaa1-Ile-Val-Glu-Xaa5-Cys-Cys-Thr-Ser-Ile-Cys-
Xaa12-Leu-Xaa14-Gln-Xaa16-Glu-Asn-Xaa19-Cys-Xaa21

[Formula 3]
(SEQ ID NO: 56)
Phe-Val-Asn-Gln-His-Leu-Cys-Gly-Ser-His-Leu-Val-
Glu-Ala-Leu-Xaa16-Leu-Val-Cys-Gly-Glu-Arg-Gly-
Phe-Xaa25-Tyr-Xaa27-Xaa28-Lys-Thr wherein:
in Formula 2, Xaa1 is glycine, Xaa5 is glutamine, Xaa12 is serine, Xaa14 is aspartic acid, Xaa16 is leucine, Xaa19 is tyrosine, and Xaa21 is asparagine; and
in Formula 3, Xaa16 is tyrosine, Xaa25 is phenylalanine, Xaa27 is threonine, and Xaa28 is proline.

2. The conjugate of claim 1, wherein X is an insulin analog comprising an amino acid sequence selected from the group consisting of SEQ ID NO: 46.

3. The conjugate of claim 1, wherein F is selected from the group consisting of a polymer, a fatty acid, a cholesterol, an albumin and a fragment thereof, an albumin-binding material, a polymer of repeating units of a particular amino acid sequence, an antibody, an antibody fragment, an FcRn-binding material, an in vivo connective tissue, a nucleotide, fibronectin, transferrin, saccharide, heparin, and elastin.

4. The conjugate of claim 1, wherein the polymer is selected from the group consisting of polyethylene glycol, polypropylene glycol, a copolymer of ethylene glycol and propylene glycol, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof.

5. The conjugate of claim 1, wherein F is an immunoglobulin Fc region.

6. The conjugate of claim 1, wherein F is an IgG Fc region.

7. The conjugate of claim 1, wherein L is selected from the group consisting of a peptide, a fatty acid, a saccharide, a polymer, a low molecular weight compound, a nucleotide, and a combination thereof.

8. The conjugate of claim 7, wherein the polymer is selected from the group consisting of polyethylene glycol, polypropylene glycol, a copolymer of ethylene glycol and propylene glycol, polyoxyethylated polyol, polyvinyl alcohol, a polysaccharide, dextran, polyvinyl ethyl ether, a biodegradable polymer, a lipid polymer, chitin, hyaluronic acid, an oligonucleotide, and a combination thereof.

9. The conjugate of claim 7, wherein the polymer has molecular weight of 1 kDa to 100 kDa.

10. The conjugate of claim 1, wherein L is polyethylene glycol.

11. The conjugate of claim 1, wherein the linker is linked to the N-terminus of the B-chain of the insulin analog or a lysine residue in the insulin analog.

12. The conjugate of claim 1, wherein F is an immunoglobulin Fc region and the linker is linked to the N-terminus of the immunoglobulin Fc region.

13. The conjugate of claim 1, wherein F is an immunoglobulin Fc region and the conjugate has a structure in which both ends of the linker are linked to the N-terminus of the B-chain of the insulin analog and the N-terminus of the immunoglobulin Fc region.

14. The conjugate of claim 1, wherein the insulin analog has a reduced binding affinity to a native insulin receptor compared to native insulin.

15. The conjugate of claim 14, wherein the binding affinity of the insulin analog to a native insulin receptor is about 10% to about 90% compared to that of native insulin.

16. The conjugate of claim 14, wherein F is an immunoglobulin Fc region, L is polyethylene glycol, and the binding affinity of the conjugate to a native insulin receptor is 0.1% to 50% compared to that of native insulin.

17. The conjugate of claim 1, wherein F is an immunoglobulin Fc region, L is polyethylene glycol, and X is an insulin analog having the same sequence as native insulin except that the 14th amino acid of the A-chain is aspartic acid.

18. A pharmaceutical composition comprising the conjugate of claim 1.

19. A method for treating diabetes in a subject in need thereof, comprising administering an effective amount of the conjugate of claim 1 or a composition thereof to the subject.

* * * * *